US009212175B2

(12) United States Patent
Fessard et al.

(10) Patent No.: US 9,212,175 B2
(45) Date of Patent: Dec. 15, 2015

(54) PHARMACEUTICAL HYPOCHOLESTEROLEMIC COMPOSITIONS

(75) Inventors: Thomas Fessard, Lausanne (CH); Dong-Bo Li, Zürich (CH); Damien Barbaras, Lausanne (CH); Susanne Wolfrum, Weiningen (CH); Erick Carreira, Zumikon (CH)

(73) Assignee: Lipideon Biotechnology AG, Zürich (CH)

( * ) Notice: Subject to any disclaimer, the term of this patent is extended or adjusted under 35 U.S.C. 154(b) by 738 days.

(21) Appl. No.: 13/254,992

(22) PCT Filed: Mar. 5, 2010

(86) PCT No.: PCT/EP2010/052821
§ 371 (c)(1),
(2), (4) Date: Oct. 18, 2011

(87) PCT Pub. No.: WO2010/100255
PCT Pub. Date: Sep. 10, 2010

(65) Prior Publication Data
US 2012/0065168 A1 Mar. 15, 2012

(30) Foreign Application Priority Data
Mar. 6, 2009 (EP) .................................... 09154496
Oct. 7, 2009 (EP) .................................... 09172395

(51) Int. Cl.
A61K 31/397 (2006.01)
C07D 405/10 (2006.01)
C07D 405/14 (2006.01)

(52) U.S. Cl.
CPC ............ *C07D 405/10* (2013.01); *C07D 405/14* (2013.01)

(58) Field of Classification Search
USPC ........................................................ 540/200
See application file for complete search history.

(56) References Cited

U.S. PATENT DOCUMENTS

| 5,633,246 | A | 5/1997 | McKittrick et al. |
| RE37,721 | E | 5/2002 | Rosenblum et al. |
| 2002/0128253 | A1 | 9/2002 | Glombik et al. |
| 2002/0137689 | A1 | 9/2002 | Glombik et al. |
| 2004/0063929 | A1 | 4/2004 | Tomiyama et al. |
| 2004/0180860 | A1 | 9/2004 | Burnett et al. |
| 2004/0180861 | A1 | 9/2004 | Burnett et al. |
| 2005/0267038 | A1 | 12/2005 | Glombik et al. |
| 2005/0267049 | A1 | 12/2005 | Goulet et al. |
| 2008/0281092 | A1 | 11/2008 | Glombik et al. |
| 2009/0264402 | A1 | 10/2009 | Jaehne et al. |
| 2010/0160282 | A1 | 6/2010 | Glombik et al. |

FOREIGN PATENT DOCUMENTS

| WO | 9302048 A1 | 2/1993 |
| WO | 9417038 A1 | 8/1994 |
| WO | 9508532 A1 | 3/1995 |
| WO | 9526334 A1 | 10/1995 |
| WO | 9535277 A1 | 12/1995 |
| WO | 9616037 A1 | 5/1996 |
| WO | 9619450 A1 | 6/1996 |
| WO | 9716455 A1 | 5/1997 |
| WO | 0250027 A1 | 6/2002 |
| WO | 0250060 A1 | 6/2002 |
| WO | 0250068 A1 | 6/2002 |
| WO | 0250090 A1 | 6/2002 |
| WO | 02066464 A1 | 8/2002 |
| WO | 04000803 A1 | 12/2003 |
| WO | 04000804 A1 | 12/2003 |
| WO | 04000805 A1 | 12/2003 |
| WO | 2004081002 A1 | 9/2004 |
| WO | 2005021495 A2 | 3/2005 |
| WO | 2005021497 A2 | 3/2005 |
| WO | 2005033100 A1 | 4/2005 |
| WO | 2005044256 A1 | 5/2005 |
| WO | 2005061451 A1 | 7/2005 |
| WO | 2005061452 A1 | 7/2005 |
| WO | 2005062824 A2 | 7/2005 |
| WO | 2006122186 A2 | 11/2006 |
| WO | 2006137782 A1 | 12/2006 |
| WO | 2006137792 A1 | 12/2006 |
| WO | 2006137793 A1 | 12/2006 |
| WO | 2006137794 A1 | 12/2006 |
| WO | 2006137796 A1 | 12/2006 |
| WO | 2006137797 A1 | 12/2006 |
| WO | 2007015161 A1 | 2/2007 |
| WO | 2007126358 A1 | 11/2007 |
| WO | 2008052658 A1 | 5/2008 |
| WO | 2008057336 A2 | 5/2008 |
| WO | 2008085300 A1 | 7/2008 |
| WO | 2008123953 A1 | 10/2008 |

OTHER PUBLICATIONS

Byrn, Stephen. Solid-State Chemistry of Drugs, 2d, Chapter 11 Hydrates and Solvates/hydrates, 233-247, 233.*
Morissette, Sherry. Adv. Drug Delivery Rev. 2004, 56, 275-300.*
Rouhi, A.M. Chem. & Eng. News, Feb. 24, 2003, 81(8), 32-35).*
NIH. NHLBI. "How can Atherosclerosis be Prevented or Delayed" Jul. 1, 2011. < http://www.nhlbi.nih.gov/health/health-topics/topics/atherosclerosis/prevention.html>.*
Badarin, Firas. Mayo clin Proc. 2009; 84(4):353-361.*
Wermuth, Camille. "Molecular Variations Based on Isoteric Replacements." The Practice of Medicinal Chemistry. Academic Press, 1996. pp. 203-237.*
Patani, George. Chem. Rev. 96, (1996) 3147-3176.*
Van Heek et al., Comparison of the activity and disposition of the novel cholesterol absorption inhibitor, SCH58235, and its glucuronide, SCH60663, British Journal of Pharmacology, 2000, pp. 1748-1754, vol. 129 (8).
Wuitschik et al., "Oxetanes as Promising Modules in Drug Discovery," Angew. Chem. Int. Ed., 2006, pp. 7736-7739, vol. 45.

* cited by examiner

*Primary Examiner* — Golam M M Shameem
*Assistant Examiner* — Laura Daniel
(74) *Attorney, Agent, or Firm* — The Webb Law Firm

(57) ABSTRACT

The present invention relates to novel azetidinone-containing compounds having a novel side-chain which is attached to the aryl ring at C4 via a C—C bond and comprises a 3,3-disubstituted oxetane ring and a polar group A, and which is useful in the treatment and prevention of atherosclerosis and for the reduction of cholesterol levels.

12 Claims, No Drawings

PHARMACEUTICAL HYPOCHOLESTEROLEMIC COMPOSITIONS

FIELD OF THE INVENTION

The present invention relates to novel oxetane-azetidinone derivatives and pharmaceutical compositions comprising said compounds alone or in combination with other active agents, methods of their production as well as their use in the treatment and prevention of atherosclerosis and for the reduction of cholesterol levels.

BACKGROUND

Atherosclerotic coronary heart disease represents the major cause for death and cardiovascular morbidity in the western world. Risk factors for atherosclerotic coronary heart disease include hypertension, diabetes mellitus, family history, male gender, and cigarette smoke as well as serum cholesterol. Elevated concentrations of serum cholesterol have been demonstrated by a number of clinical studies to be a major contributing factor in the development and progression of atherosclerosis, which is characterized by the formation of cholesterol-containing plaques in the aorta and lesser arteries. In mammals, about ⅓ of the serum cholesterol is derived from exogenous dietary sources, which enters the body through absorption in the intestine, and ⅔ of the serum cholesterol are derived through endogenous de novo synthesis in the liver involving a complex set of enzyme-catalyzed reactions and regulatory mechanisms.

It has been reported in the literature that intestinal cholesterol absorption is an energy-independent, protein-mediated process rather than a passive diffusion process. Research efforts that focused on identifying classes of compounds that are able to interfere with the above-described processes have revealed that compound classes having a 2-azetidinone may be useful in lowering cholesterol and/or in inhibiting the formation of cholesterol-containing lesions in mammalian arterial walls.

A non-exhaustive list of such azetidinones can be found in WO 93/02048, WO 94/17038, WO 95/08532, WO 95/26334, U.S. Pat. No. 5,633,246, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO 04/000805, WO 04/081002, WO 05/021495, WO 05/021497, WO 05/033100, WO 05/044256, WO 05/044256, WO 05/062824, WO 05/061451, WO 05/061452, US 20040180860, US 20040180861, US 20050267049, U.S. Pat. No. RE 37,721, WO 2006/122186, WO 2006/137782, WO 2006/137792, WO 2006/137793, WO 2006/137794, WO 2006/137796, WO 2006/137797, WO 2007/015161, WO 2007/126358, WO 2008/052658, WO 2008/123953, WO 2008/085300, WO 2008/057336.

Extensive studies on the 2-azetidinones have shown that their activity was highly dependent on the nature and configuration of the various sidechains attached to the central β-lactam motif. These findings resulted in the development of the most prominent representative of the 2-azetidinones, Ezetimibe (also known under trade names Zetia™ and Ezetrol®), which is in use as a cholesterol-lowering drug in monotherapy and in dual therapy combined with a statin.

However, there are also side effects associated with this first generation of 2-azetidinones, which may include absorption and metabolization upon administration into the pharmalogically active glucuronide (van Heek, M. et al. *Br. J. Pharmacol.* 2000, 129, 1748-1754) as well as as allergic reactions, e.g. rash and angiodema. More recently a higher risk of developing cancer has been reported in specific cases.

Such drawbacks may be caused by e.g. the hydrolytic instability of the 2-azetidinone ring scaffold and/or the systemic nature of some of those compounds, which typically act as a prodrug and cause effective inhibition of the uptake of cholesterol in the small intestine only after absorption and metabolization into the pharmalogically active glucuronide (van Heek, M. et al. *Br. J. Pharmacol.* 2000, 129, 1748-1754).

Clearly, there is still a great need for effective inhibitors of dietary cholesterol transport or uptake through the gut membrane which show minimal drug-drug interactions and off-target pharmacology and thus have an improved safety/toxicology profile.

Applicants have now found that high pharmacological activity, i.e. inhibitory activity, can be achieved by linking the pharmacophore moiety of the molecule to a novel class of side-chains which confers beneficial toxicology and pharmacologic profile to the compounds of the invention. In particular, this side-chain intends to render the resulting bioconjugate poorly bioavailable and therefore may limit the risk caused by liver exposure. Thus, the compounds of the present invention with the structural characteristics as depicted hereinafter are able to inhibit cholesterol absorption, while overcoming the above described disadvantages of compounds known in the art.

SUMMARY OF THE INVENTION

The present invention relates to novel hypocholesterolemic compounds useful in the treatment and prevention of atherosclerosis and for the reduction of cholesterol levels as well as to pharmaceutical compositions comprising said compounds alone or in combination with other active agents.

In particular, the present invention relates to azetidinone compounds comprising a novel sidechain attached to C4-aryl of the β-lactam ring which is characterized by a C—C linkage to the lactams ring and the presence of an oxetane ring and a polar group.

Thus in a first aspect the present invention relates to compounds of formula I, or a pharmaceutically acceptable salt or solvate thereof,

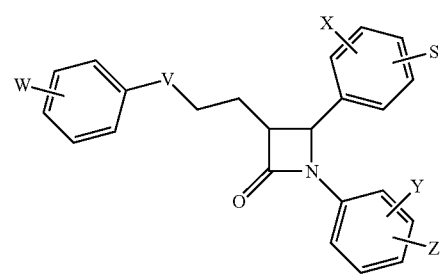

wherein
W, X and Y represent, independently of each other, H, —(C1-C10)alkyl, —OR$_1$, —NR$_2$R$_3$, -aryl, halogen, —CF$_3$, wherein R$_1$, R$_2$, R$_3$ represent independently of each other H, (C1-10)alkyl or aryl;
Z represents H, —(C1-C10)alkyl, —(C1-C10)alkenyl, —(C1-C10)alkynyl, aryl, or a polar group A selected from halogen, epoxy, —COR$_6$, —COOR$_7$, —NR$_8$R$_9$, —N$^+$R$_8$R$_9$R$_{10}$, —OR$_{11}$, —CONR$_{12}$R$_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl or heteroaryl, or combinations thereof such as —(C1-C10)alkylaryl, —(C1-C10)alkenyl-aryl, —(C1-C10)alkynyl-aryl, or one of —(C1-C10)alkyl, —(C1-C10)alkenyl, —(C1-C10)alkynyl, aryl substituted by at least one polar group A;

V represents —$CH_2$—, —CH(OH)—, —C(=O)—, —O—, $NR_4$, —C($CH_2OCH_2$)— wherein $R_4$ represents H, (C1-C10)alkyl or aryl;

S is a sidechain of formula II

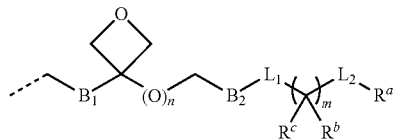

wherein the dotted line represents the linkage to the group of formula I;

$B_1$ represents (C1-C3)alkyl or —$(CH_2)_q$—$NR_5$—, wherein $R_5$ is H or (C1-C6)alkyl, benzyl or aryl and q is 0, 1, 2, or 3;

$B_2$ represents —C(O)$NR^d$—, —C(O)O—, aryl or heteroaryl;

$R^a$, $R^d$ represent (i) independently of each other H, (C1-C10) alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or combinations thereof such as —(C1-C10)alkyl-aryl, —(C1-C10)alkyl-cycloalkyl, or one of —(C1-C10)alkyl, cycloalkyl, aryl substituted by at least one polar group A, or (ii) $R^a$ and $R^d$ form together a N-containing 5- or 6-membered heteroaryl or heterocycloalkyl;

$L_1$, $L_2$ represent independently of each other a covalent bond, a 5- or 6-membered arylgroup or a group —$(CH_2)_p$—, wherein p is 1, 2 or 3;

$R^b$, $R^c$ represent (i) independently of each other H, (C1-C10) alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or combinations thereof such as —(C1-C10)alkyl-aryl, —(C1-C10)alkylcycloalkyl, or one of —(C1-C10)alkyl, cycloalkyl, aryl substituted by at least one polar group A, or (ii) $R^b$ and $R^c$ form together a (C3-C6)cycloalkyl or (C3-6)heterocycloalkyl, m is 0, 1 or 2;
n is 0 or 1;
with the proviso that at least one of groups $R^a$, $R^b$, $R^c$, $R^d$ is a polar group A.

In a further aspect the invention is directed towards a pharmaceutical composition comprising a therapeutically effective amount of a compound of the invention with a pharmaceutically acceptable carrier, optionally in combination with one or more additional active agents.

In a further aspect the invention is directed towards the use of a compound or a pharmaceutical composition of the invention in the treatment or prevention of atheriosclerosis or for the reduction of cholesterol levels.

In yet a further aspect the invention is directed towards a kit comprising a pharmaceutical composition of the invention for the use in the treatment or prevention of artheriosclerosis or for the reduction of cholesterol levels.

In yet a further aspect the invention is directed towards a method for the treatment or prevention of artheriosclerosis or for the reduction of cholesterol levels comprising administering to a subject in need of such treatment an effective amount of a compound or a pharmaceutical composition of the invention.

DETAILED DESCRIPTION OF THE INVENTION

The present invention relates to novel azetidinone-containing compounds having a novel side-chain which is attached to the aryl ring at C4 via a C—C bond and comprises a 3,3-disubstituted oxetane ring and a polar group A (hereinafter also called compounds of the invention), and which are useful in the treatment and prevention of atherosclerosis and for the reduction of cholesterol levels.

Unless stated otherwise, the following definitions apply:

The term "alkyl" or "(C1-10)alkyl" used alone or in combination with other groups should be understood to include straight chain and branched hydrocarbon groups having from 1 to 10, preferably 1 to 6, more preferably from 1 to 3 carbon atoms. Alkyl groups may be optionally substituted with one or more substituents. Non-limiting examples of suitable (C1-10)alkyl groups include methyl, ethyl, n-propyl, isopropyl, n-butyl, t-butyl, n-pentyl, fluoromethyl and trifluoromethyl.

The term "alkenyl" refers to an alkyl group containing at least one carbon-carbon double bond. Alkenyl groups may be optionally substituted with one or more substituents.

The term "alkynyl" refers to an alkyl group containing at least one carbon-carbon triple bond. Alkynyl groups may be optionally substituted with one or more substituents.

The optional substituents of alkyl, alkenyl and alkynyl groups may be the same or different, and are independently selected from H, (C1-10)alkyl, —OR", —NR"R'", —$N^+(R")_2R'"$, —OCOR", —COOR", —CONR"R'", —CH=CHCOOR", —$CF_3$, —CN, —$NO_2$, or halogen, wherein R" and R'" represent H or (C1-10)alkyl.

The term "branched" should be understood to represent a linear straight chain hydrocarbon group having one or more lower alkyl groups such as methyl, ethyl or propyl, attached to it.

The term "halogen" (or "hal") should be understood to include fluoro, chloro, bromo, iodo, preferably fluoro and chloro, most preferably fluoro.

The term "polyhydroxy" refers to linear, cyclic or branched (C1-C10)alkyl chains being substituted by two to ten hydroxy groups at the same or different, preferably different C-atoms. In a preferred embodiment polydroxy groups may be characterized by the formula —$(CH(OH))_r$—, wherein r is 2 to 10, more preferably 2, 3, 4, 5 or 6.

The term "cycloalkyl" unless defined otherwise refers to a saturated monocyclic or bicyclic ring system having 3 to 10, preferably 3, 4, 5, 6 or 10, more preferably 3, 4, 5 or 6 ring atoms. Preferred cycloalkyl groups include cyclopropyl, cyclobutyl, cyclopentyl, cyclohexyl, norbornyl and the like.

The term "alkyl-cycloalkyl" (or "—(C1-C10)alkyl-cycloalkyl") refers to a radical wherein alkyl (or (C1-10)alkyl)

and cycloalkyl have the meanings as defined above. Illustrative examples of an alkyl-cycloalkyl group or radical include 3-methylcyclohexyl and 4-hexylcycloheptyl.

The term "heterocycloalkyl" unless defined otherwise refers to a cycloalkyl group as defined above, wherein one or more of the atoms in the ring system, preferably 1 to 3 is/are replaced by heteroatoms chosen from the group consisting of O, S, and N. Both uncharged as well as charged heteroaryls are included, thus for example "N" encompasses —$NR_x$—, wherein $R_x$ is H or (C1-10)alkyl (uncharged heteroaryl) and —$N^+(R_x)_2$— where $R_x$ is (C1-10)alkyl (charged heteroaryl). Preferred heterocycloalkyl include pyrrolidine, piperidine, piperazine, 1-methylpiperazine, oxazines, such as morpholine, thiazines and the like.

The term "aryl" unless defined otherwise should be understood to include a monocyclic or bicyclic, aromatic ring system having 5 to 10, preferably 5, 6 or 10, more preferably 5 or 6 ring atoms. Non-limiting examples of suitable aryl groups include phenyl, (1- or 2-)naphthyl or tetraline groups, most preferably phenyl groups.

The term "alkylaryl" (or "(C1-10)alkylaryl") refers to a radical wherein alkyl (or (C1-10)alkyl) and aryl have the meanings as defined above. Illustrative examples of an alkylaryl group or radical include benzyl, 2-phenylethyl, 3-phenylpropyl, 4-phenylbutyl, 3-methyl-3-phenylpropyl, 1-naphthylmethyl, 1-naphthylethyl.

The term "alkenylaryl" (or "(C1-10)alkenylaryl") refers to a radical wherein alkenyl (or (C1-10)alkenyl) and aryl have the meanings as defined above. Particular examples of an alkenylaryl group or radical are vinyl benzene and -(3-(4-sulfonophenyl)prop-1-enyl).

The term "alkynylaryl" (or "(C1-10)alkynylaryl") refers to a radical wherein alkynyl (or (C1-10)alkynyl) and aryl have the meanings as defined above. A particular example of an alkynylaryl group or radical is -(3-(4-sulfonophenyl)prop-1-ynyl).

The term "heteroaryl" unless defined otherwise should be understood to include an aromatic ring system of 5 to 10, preferably 5, 6 or 10, more preferably 5 or 6 ring atoms, in which one or more of the atoms in the ring system is/are atoms other than carbon, for example nitrogen, oxygen or sulfur. Preferably, the aromatic heteroaryl is a 5- or 6-membered aromatic ring having 1 to 3 heteroatoms selected from N, O, S, preferably N and O, and benzo-fused derivatives thereof. Examples of suitable 6-membered heteroaryl groups include pyridine, pyrimidine, pyrazine, pyridazine and the like. Examples of useful 5-membered aromatic heteroaryls include furan, pyrrole, triazole, thiazole, isothiazole, imidazole, pyrazole, oxazole and isoxazole. Useful bicyclic groups are benzo-fused ring systems derived from the aromatic heteroaryls named above, e.g., quinoline, phthalazine, quinazoline, benzofuran, phthaleimide and indole. Most preferred examples are pyridine, pyrimidine, oxazole, thiazole, imidazole, triazole, pyrazole, and phthaleimide.

The cyclic groups aryl, heteroaryl, cycloalkyl and heterocycloalkyl can be substituted with one or more substituents R', preferably one, two or three substituents R', which may be the same or different, and are independently selected from H, (C1-10)alkyl, —OR", —NR"R'", —$N^+(R")_2$R'", —OCOR", —COOR", —CONR"R'", —CH=CHCOOR", —$CF_3$, —CN, —$NO_2$, or halogen, wherein R" and R'"represent H or (C1-10)alkyl. Unless defined otherwise R' represents preferably one or more substituents, preferably one, two or three substituents, selected from H, C1-10)alkyl, —OH, —O(C1-10)alkyl, —NR"R'", —$N^+(R")_2$R'", —CN, or halogen. For example, if R' represents (C1-10)alkyl, alkylaryl groups such as benzyl, phenethyl and the like, alkylheteroaryl groups such as 2-furylmethyl, 2-thienylmethyl, 2-(1H-indol-3-yl)ethyl and the like, alkylcycloalkyl groups such as cyclohexylmethyl, cyclopentylpropyl, and the like, and alkylheterocycloalkyl groups such as 2-(1-pyrrolidinyl)ethyl, 4-morpholinylmethyl, (1-methyl-4-piperidinyl)methyl and the like, are included. Charged alkylheterocycloalkyls are included as well, for example when the (C1-10)alkyl group is attached to e.g. an N-ring atom. The substituents R' may be in any position.

For example in monosubstituted phenyl residues the substituent can be located in the ortho-position, the meta-position or the para-position, preferably in the para-position. If phenyl is substituted twice, the substituents can be in the ortho/meta-position (all possibilities), the ortho/para-position, the ortho/ortho-position, the meta/meta-position, or the meta/para-position. In substituted heteroaryl or heterocycloalkyl groups, the substituent may reside on a carbon atom or a heteroatom, such that charged groups are contemplated as well, e.g. N-methyl morpholinium and the like.

The term "polar group" should be understood to include any polar moiety which enhances and thus imparts impermeability to the compounds of the invention. This includes uncharged and charged (both positively and negatively) groups. Typical examples of such moieties include halogen, carbonyl groups including carboxylic acids and carboxylic amides, amine and amino acid residues, glucuronides, polyhydroxy groups and glucamine derivatives, 2,3-dihydroxy propoxy groups, tartrate groups, N-(2-Hydroxyethyl)-iminodiacetic acid groups, heteroaryl groups (e.g. pyridine, oxazole, isoxazole, triazole and tetrazolium (salt) groups), phosphate groups, phosphonate groups, sulfate groups (e.g. R—O—$SO_3$— and $R_2$N—$SO_3$-groups), sulfonate groups R—$SO_2$—O—R (which include e.g. sulfonic acid, sulfonic salts and sulfonic esters), sulfonyl groups R—$SO_2$R, which include e.g. sulfonamides —RN—$SO_2$— (such as —$NR_{14}SO_2R_{15}$ or —$SO_2NR_{16}R_{17}$, wherein $R_{14}$, $R_{15}$, $R_{16}$, $R_{17}$ are independently of each other H, (C1-C10)alkyl, aryl, or heteroaryl), isomers of salicylic acid (all combinations of disubstituted phenyl with OH and COOH substituents), alkylamine groups —$NR_8R_9$, alkylammonium or arylammonium groups —$N^+R_8R_9R_{10}$ and the corresponding quaternary ammonium salts and derivatives thereof. Preferred groups include carboxylic acid groups, aminoacid residues, polyhydroxy groups, tartrate groups, N-(2-Hydroxyethyl)-iminodiacetic acid groups, phosphate or phosphonate groups, sulfate, sulfonate, sulfonyl or sulfonamide groups, alkylamine groups, alkylammonium or arylammonium groups, and derivatives thereof, more preferably carboxylic acid groups, aminoacid residues, phosphonate groups, sulfonates, sulfonyl or sulfonamide groups, alkylammonium groups and derivatives thereof.

The term "alkylammonium" as used herein encompasses mono-, di- and tri-alkyl ammonium groups wherein alkyl groups contain from 1 to 10 carbon atoms and are either in non-cyclic form (i.e. single chains) or form together with the N-group an N-containing heterocycle, as well as cycloalkyl groups containing from 3 to 6 carbon atoms. The alkylammonium group includes, for example, mono-, di- and tri-methyl, ethyl, propyl, isopropyl, butyl, pentyl, hexyl, t-butyl, t-pentyl ammonium groups, cyclopropyl ammonium, cyclobutylethylammonium, cyclopentylmethyl ammonium, cyclohexylammonium, as well as a quaternary ammonium group of e.g. piperazine, morpholine, piperidine and the like.

The term "arylammonium" as used herein encompasses preferably a cationic derivative of an aryl-substituted amine or an aryl-bonded amine. Examples for an aryl-substituted amine (or ammonium) includes e.g. aniline and substituted anilines such as the mono-, di- and tri-halo, nitro, methoxy, methyl, and ethyl anilines (or unsubstituted or substituted phenylammonium), and specifically cationic derivatives derived from the primary phenyl amines such as aniline, methoxyaniline, ethoxyaniline, o,m,p-toluidine, o,m,p-chloroaniline, o,m,p-anisidine, o, m, and p-nitroaniline, 2,4-dichloroaniline, 3,5-dichloroaniline, 2,5-diiodoaniline, o, m, and p-bromoaniline and the like. Examples of a cationic derivative of an aryl-bonded amine include an ammonium group of e.g. imidazole, pyridine, pyrimidine, pyrazole, chinoline, and the like.

A skilled person will know that, if the polar moiety is a positively charged group, a suitable counterion will be derived from an organic or inorganic acid. Such counterions include halide (such as chloride, bromide, fluoride, iodide), sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. If the polar moiety is a negatively charged groups, a suitable counterion will be selected from sodium, ammonium, barium, calcium, copper, iron, lithium, potassium and zinc, and the like.

In one embodiment the polar group is a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl or heteroaryl.

For any one of groups $R^a$, $R^b$, $R^c$ and $R^d$ group A may represent group A1 selected from —$COR_6$, —$COOR_7$, —$NR_8R_9$, —$N^+R_8R_9R_{10}$, —$OR_{11}$, —$CONR_{12}N_{13}$, polyhydroxy, sulfonate group, sulfonamides (such as $NR_{14}SO_2R_{15}$ or —$SO_2NR_{16}R_{17}$), phosphonate group, piperazinyl, piperidinyl, pyrrolidinyl, morpholinyl groups or a combination thereof such as -piperazine-$SO_3H$, —$N(CH_2CH_2)_2N^+R_{14}R_{15}$, wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$ are independently of each other H or (C1-C10)alkyl.

For group Z group A may preferably represent a group A2 selected from halogen, —$COR_6$, —$COOR_7$, —$NR_8R_9$, —$N^+R_8R_9R_{10}$, —$OR_{11}$, —$CONR_{12}R_{13}$, —$SO_3H$, —$NR_{14}SO_2R_{15}$, —$SO_2NR_{16}R_{17}$, —$SO_2R_{18}$, polyhydroxy, heteroaryl, or heterocycloalkyl, wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ are independently of each other H, —(C1-C10)alkyl, aryl or heteroaryl, and wherein the heteroaryl is selected from pyridine, pyrimidine, oxazole, thiazole, imidazole, triazole, pyrazole, and phthaleimide.

Thus, preferred combinations of group Z (represented by "—(C1-C10)alkyl, —(C1-C10)alkenyl, —(C1-C10)alkynyl, aryl substituted by at least one polar group A") include —(C1-C10)alkyl-$COR_6$, —(C1-C10)alkenyl-$COR_6$, —(C1-C10)alkynyl-$COR_6$, —(C1-C10)alkyl-$COOR_7$, —(C1-C10)alkenyl-$COOR_7$, —(C1-C10)alkynyl-$COOR_7$, —(C1-C10)alkyl-$NR_8R_9$, —(C1-C10)alkenyl-$NR_8R_9$, —(C1-C10)alkynyl-$NR_8R_9$, —(C1-C10)alkyl-$N^+R_8R_9R_{10}$, —(C1-C10)alkenyl-$N^+R_8R_9R_{10}$, —(C1-C10)alkynyl-$N^+R_8R_9R_{10}$, —(C1-C10)alkyl-$OR_{11}$, —(C1-C10)alkenyl-$OR_{11}$, —(C1-C10)alkynyl-$OR_{11}$, —(C1-C10)alkyl-$CONR_{12}N_{13}$, —(C1-C10)alkenyl-$CONR_{12}N_{13}$, —(C1-C10)alkynyl-$CONR_{12}N_{13}$, —(C1-C10)alkyl-$SO_3H$, —(C1-C10)alkenyl-$SO_3H$, —(C1-C10)alkynyl-$SO_3H$, —(C1-C10)alkyl-$SO_2R_{18}$, —(C1-C10)alkenyl-$SO_2R_{18}$, —(C1-C10)alkynyl-$SO_2R_{18}$, —(C1-C10)alkyl $SO_2NR_{16}R_{17}$, —(C1-C10)alkenyl-$SO_2NR_{16}R_{17}$, —(C1-C10)alkynyl-$SO_2NR_{16}R_{17}$, —(C1-C10)alkyl-$NR_{14}SO_2R_{15}$, —(C1-C10)alkenyl-$NR_{14}SO_2R_{15}$, —(C1-C10)alkynyl-$NR_{14}SO_2R_{15}$, —(C1-10)alkyl-heteroaryl, —(C1-C10)alkenyl-heteroaryl, —(C1-C10)alkynyl-heteroaryl, —(C1-10)alkyl-heterocycloalkyl, —(C1-C10)alkenyl-heterocycloalkyl, —(C1-C10)alkynyl-heterocycloalkyl wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ are independently of each other H, —(C1-C10)alkyl, aryl or heteroaryl, and wherein the heteroaryl is selected from pyridine, pyrimidine, oxazole, thiazole, imidazole, triazole, pyrazole, and phthaleimide.

More preferred combinations of group Z (represented by "—(C1-C10)alkyl, —(C1-C10)alkenyl, —(C1-C10)alkynyl, aryl substituted by at least one polar group A") include, —(C1-C10)alkyl-$COOR_7$, —(C1-C10)alkenyl-$COOR_7$, —(C1-C10)alkynyl-$COOR_7$, —(C1-C10)alkyl-$NR_8R_9$, —(C1-C10)alkenyl-$NR_8R_9$, —(C1-C10)alkynyl-$NR_8R_9$, —(C1-C10)alkyl-$N^+R_8R_9R_{10}$, —(C1-C10)alkenyl-$N^+R_8R_9R_{10}$, —(C1-C10)alkynyl-$N^+R_8R_9R_{10}$, —(C1-C10)alkyl-$OR_{11}$, —(C1-C10)alkenyl-$OR_{11}$, —(C1-C10)alkynyl-$OR_{11}$, —(C1-C10)alkyl-$SO_3H$, —(C1-C10)alkenyl-$SO_3H$, —(C1-C10)alkynyl-$SO_3H$, —(C1-C10)alkyl-$SO_2R_{18}$, —(C1-C10)alkenyl-$SO_2R_{18}$, —(C1-C10)alkynyl-$SO_2R_{18}$, —(C1-C10)alkyl-$SO_2NR_{16}R_{17}$, —(C1-C10)alkenyl-$SO_2NR_{16}R_{17}$, —(C1-C10)alkynyl-$SO_2NR_{16}R_{17}$, —(C1-C10)alkyl-$NR_{14}SO_2R_{15}$, —(C1-C10)alkenyl-$NR_{14}SO_2R_{15}$, —(C1-C10)alkynyl-$NR_{14}SO_2R_{15}$, wherein $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ are independently of each other H, —(C1-C10)alkyl, aryl or heteroaryl, and wherein the heteroaryl is selected from pyridine, pyrimidine, oxazole, thiazole, imidazole, triazole and pyrazole.

It is further understood that all isomers, including enantiomers, stereoisomers, rotamers, tautomers and racemates of the compounds of formula I are contemplated as being part of this invention. The invention includes stereoisomers in optically pure form and in admixture, including racemic mixtures. Isomers can be prepared using conventional techniques, either by reacting optically pure or optically enriched starting materials or by separating isomers of a compound of formula I. In a preferred embodiment the stereochemistry in the central ring is such that the substituents at the 3- and 4-position are in trans configuration to each other.

More specifically, the present invention relates to a compound according to formula I or a pharmaceutically acceptable salt or solvate thereof,

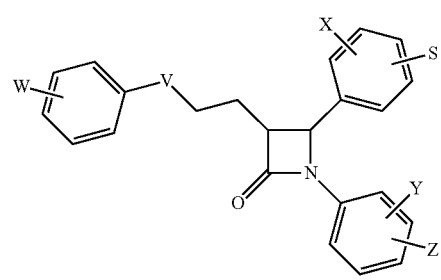

I wherein
W, X and Y represent, independently of each other, H, —(C1-C10)alkyl, —OH, —O(C1-C10)alkyl, -aryl, halogen, —$CF_3$;
Z represents H, —(C1-C10)alkyl, —(C1-C10)alkenyl, —(C1-C10)alkynyl, aryl, or a polar group A selected from halogen, epoxy, —$COR_6$, —$COOR_7$, —$NR_8R_9$, —N⁺R₈R₉R₁₀, —OR₁₁, —CONR₁₂N₁₃, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6, R_7, R_8, R_9, R_{10}, R_{11}, R_{12}, R_{13}$ are independently of each other H, (C1-C10)alkyl, aryl, or heteroaryl, or combinations thereof such as —(C1-C10)alkyl-aryl, —(C1-C10)alkenyl-aryl, —(C1-C10)alkynyl-aryl, or one of —(C1-C10)alkyl, —(C1-C10)alkenyl, —(C1-C10)alkynyl, aryl substituted by at least one polar group A;

V represents —CH₂—, —CH(OH)—, —C(=O)—, —O—, NR₄, —C(CH₂OCH₂)— wherein $R_4$ represents H, (C1-C10)alkyl or aryl;

S is a sidechain of formula II

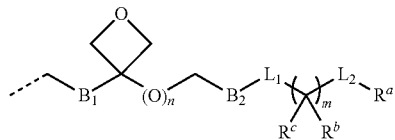

wherein the dotted line represents the linkage to the group of formula I;

$B_1$ represents (C1-C3)alkyl or —(CH₂)$_q$—NR₅—, wherein $R_5$ is H or (C1-C6)alkyl, benzyl or aryl and q is 0, 1, 2, or 3;

$B_2$ represents —C(O)NR$^d$—, —C(O)O—, aryl or heteroaryl;

$R^a$, $R^d$ represent (i) independently of each other H, (C1-C10) alkyl, cycloalkyl, aryl, or a polar group A selected from halogen, epoxy, —COR₆, —COOR₇, —NR₈R₉, —N⁺R₈R₉R₁₀, —OR₁₁, —CONR₁₂N₁₃, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6, R_7, R_8, R_9, R_{10}, R_{11}, R_{12}, R_{13}$ are independently of each other H, (C1-C10)alkyl, aryl, or heteroaryl, or combinations thereof such as —(C1-C10)alkyl-aryl, —(C1-C10)alkylcycloalkyl, or one of —(C1-C10)alkyl, cycloalkyl, aryl substituted by at least one polar group A, or (ii) $R^a$ and $R^d$ form together a N-containing 5- or 6-membered heteroaryl or heterocycloalkyl;

$L_1, L_2$ represent independently of each other a covalent bond, a 5- or 6-membered arylgroup or a group —(CH₂)$_p$—, wherein p is 1, 2 or 3;

$R^b, R^c$ represent (i) independently of each other H, (C1-C10) alkyl, cycloalkyl, aryl, or a polar group A selected from halogen, epoxy, —COR₆, —COOR₇, —NR₈R₉, —N⁺R₈R₉R₁₀, —OR₁₁, —CONR₁₂N₁₃, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6, R_7, R_8, R_9, R_{10}, R_{11}, R_{12}, R_{13}$ are independently of each other H, (C1-C10)alkyl, aryl, or heteroaryl, or combinations thereof such as —(C1-C10)alkyl-aryl, —(C1-C10)alkylcycloalkyl, or one of —(C1-C10)alkyl, cycloalkyl, aryl substituted by at least one polar group A, or (ii) $R^b$ and $R^c$ form together a (C3-C6)cycloalkyl or (C3-6)heterocycloalkyl, m is 0, 1 or 2;

n is 0 or 1;

with the proviso that at least one of groups $R^a, R^b, R^c, R^d$ is a polar group A.

It is understood that $R^a$ and $R^d$ may only form together a N-containing 5- or 6-membered heteroaryl or heterocycloalkyl if $B_2$ equals —C(O)NR$^d$—.

In a specific embodiment the polar group A in groups $R^a$ and $R^d$ is a polar group A1 selected from —COR₆, —COOR₇, —NR₈R₉, —N⁺R₈R₉R₁₀, —OR₁₁, —CONR₁₂N₁₃, polyhydroxy, sulfonate group, sulfonamides (such as NR₁₄SO₂R₁₅ or —SO₂NR₁₆R₁₇), phosphonate group, piperazinyl, piperidinyl, pyrrolidinyl, wherein $R_6, R_7, R_8, R_9, R_{10}, R_{11}, R_{12}, R_{13}, R_{14}, R_{15}, R_{16}, R_{17}$ are independently of each other H or (C1-C10)alkyl.

As indicated above, one polar group has to be present in either $R^a, R^b, R^c, R^d$ of the side chain S. Thus, in one embodiment, $R^b$ and $R^c$ are independently of each other H, (C1-C10) alkyl, aryl, cycloalkyl, aryl, heteroaryl or form together a (C3-C6)cycloalkyl or (C3-6)heterocycloalkyl and $R^d$ is H, (C1-C10)alkyl, cycloalkyl, aryl, heteroaryl; and $R^a$ represents a polar group A, preferably a polar group A1.

In another embodiment $R^a$ and $R^d$ form together a N-containing 5- or 6-membered heteroaryl or heterocycloalkyl; and $R^b$ and $R^c$ represent independently of each other H, (C1-C10) alkyl, cycloalkyl, aryl, or a polar group A or combinations thereof such as —(C1-C10)alkyl-aryl, —(C1-C10)alkyl-cycloalkyl, or one of —(C1-C10)alkyl, cycloalkyl, aryl substituted by at least one polar group A, preferably a polar group A1, with the proviso that at least one $R^b$ and $R^c$ comprises a polar group A, preferably a polar group A1. It is understood that for m=2 all four substituents $R^b$ and $R^c$ can be selected independently of each other. Preferred N-containing 5- or 6-membered heteroaryl or heterocycloalkyl include unsubstituted or substituted pyridine, pyrimidine, imidazole, triazole, pyrazole, pyrrolidine, piperidine.

In yet another embodiment $R^b, R^c, R^d$ are independently of each other H, (C1-C10)alkyl, cycloalkyl, aryl, or a polar group A and combinations thereof such as —(C1-C10)alkyl-aryl, —(C1-C10)alkyl-cycloalkyl, or one of —(C1-C10) alkyl, cycloalkyl, aryl substituted by at least one polar group A, preferably a polar group A1 and $R^a$ is a polar group A, preferably a polar group A1.

In yet other embodiments either two or three or all of groups $R^a, R^b, R^c, R^d$ are a polar group A, preferably a polar group A1.

Z represents preferably H, —(C1-C10)alkyl, —(C1-C10)alkenyl, —(C1-C10)alkynyl, aryl, or a polar group A2 selected from halogen, —COR₆, —COOR₇, —NR₈R₉, —N⁺R₈R₉R₁₀, —OR₁₁, —CONR₁₂R₁₃, —SO₃H, —NR₁₄SO₂R₁₅, —SO₂NR₁₆R₁₇, —SO₂R₁₈, polyhydroxy, heteroaryl, or heterocycloalkyl, or combinations thereof such as —(C1-C10)alkyl-aryl, —(C1-C10)alkenyl-aryl, —(C1-C10)alkynyl-aryl, —(C1-C10)alkyl COR₆, —(C1-C10)alkenyl-COR₆, —(C1-C10)alkynyl-COR₆, —(C1-C10)alkyl-COOR₇, —(C1-C10)alkenyl-COOR₇, —(C1-C10)alkynyl-COOR₇, —(C1-C10)alkyl-NR₈R₉, —(C1-C10)alkenyl-NR₈R₉, —(C1-C10)alkynyl-NR₈R₉, —(C1-C10)alkyl-N⁺R₈R₉R₁₀, —(C1-C10)alkenyl-N⁺R₈R₉R₁₀, —(C1-C10)alkynyl-N⁺R₈R₉R₁₀, —(C1-C10)alkyl-OR₁₁, —(C1-C10)alkenyl-OR₁₁, —(C1-C10)alkynyl-OR₁₁, —(C1-C10)alkyl-CONR₁₂N₁₃, —(C1-C10)alkenyl-CONR₁₂N₁₃, —(C1-C10)alkynyl-CONR₁₂N₁₃, —(C1-C10)alkyl-SO₃H, —(C1-C10)alkenyl-SO₃H, —(C1-C10)alkynyl-SO₃H, —(C1-C10)alkyl-SO₂R₁₈, —(C1-C10)alkenyl-SO₂R₁₈, —(C1-C10)alkynyl-SO₂R₁₈, —(C1-C10)alkyl-SO₂NR₁₆R₁₇, —(C1-C10)alkenyl-SO₂NR₁₆R₁₇, —(C1-C10)alkynyl-SO₂NR₁₆R₁₇, —(C1-C10)alkyl-NR₁₄SO₂R₁₅, —(C1-C10)alkenyl-NR₁₄SO₂R₁₅, —(C1-C10)alkynyl-NR₁₄SO₂R₁₅, —(C1-10)alkyl-heteroaryl, —(C1-C10)alkenyl-heteroaryl, —(C1-C10)alkynyl-heteroaryl, —(C1-10)alkyl-heterocycloalkyl, —(C1-C10)alkenyl-heterocycloalkyl, —(C1-C10) alkynyl-heterocycloalkyl wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ are independently of each other H, —(C1-C10)alkyl, aryl or heteroaryl, and wherein the heteroaryl is selected from pyridine, pyrimidine, oxazole, thiazole, imidazole, triazole, pyrazole, and phthaleimide.

More preferably Z represents H, —(C1-C10)alkyl, —(C1-C10)alkenyl, —(C1-C10)alkynyl, aryl, or a polar group A2 selected from halogen, —$COR_6$, —$COOR_7$, —$NR_8R_9$, —$N^+R_8R_9R_{10}$, —$OR_{11}$, —$CONR_{12}R_{13}$, —$SO_3H$, —$NR_{14}SO_2R_{15}$, —$SO_2NR_{16}R_{17}$, —$SO_2R_{18}$, polyhydroxy, heteroaryl, or heterocycloalkyl, or combinations thereof such as —(C1-C10)alkyl-aryl, —(C1-C10)alkenyl-aryl, —(C1-C10)alkynyl aryl, —(C1-C10)alkyl-$COOR_7$, —(C1-C10)alkenyl-$COOR_7$, —(C1-C10)alkynyl-$COOR_7$, —(C1-C10)alkyl-$NR_8R_9$, —(C1-C10)alkenyl-$NR_8R_9$, (C1-C10)alkynyl-$NR_8R_9$, —(C1-C10)alkyl-$N^+R_8R_9R_{10}$, —(C1-C10)alkenyl-$N^+R_8R_9R_{10}$, —(C1-C10)alkynyl-$N^+R_8R_9R_{10}$, —(C1-C10)alkyl-$OR_{11}$, —(C1-C10)alkenyl-$OR_{11}$, —(C1-C10)alkynyl-$OR_{11}$, —(C1-C10)alkyl-$SO_3H$, —(C1-C10)alkenyl-$SO_3H$, —(C1-C10)alkynyl-$SO_3H$, —(C1-C10)alkyl-$SO_2R_{18}$, —(C1-C10)alkenyl-$SO_2R_{18}$, —(C1-C10)alkynyl-$SO_2R_{18}$, —(C1-C10)alkyl-$SO_2NR_{16}R_{17}$, —(C1-C10)alkenyl-$SO_2NR_{16}R_{17}$, —(C1-C10)alkynyl-$SO_2NR_{16}R_{17}$, —(C1-C10)alkyl-$NR_{14}SO_2R_{15}$, —(C1-C10)alkenyl-$NR_{14}SO_2R_{15}$, —(C1-C10)alkynyl-$NR_{14}SO_2R_{15}$, wherein $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ are independently of each other H, —(C1-C10)alkyl, aryl or heteroaryl, and wherein the heteroaryl is selected from pyridine, pyrimidine, oxazole, thiazole, imidazole, triazole and pyrazole.

$B_1$ represents preferably —$CH_2$— or —$CH_2$—$CH_2$—$NR_5$—, wherein $R_5$ is H, (C1-C6)alkyl, benzyl or aryl.

In one embodiment $B_1$ represents —$CH_2$— and n=1. In another embodiment $B_1$ represents —$CH_2$—$CH_2$—$NR_5$—, wherein $R_5$ is H, (C1-C6)alkyl, benzyl or aryl and n=0.

$B_2$ represents preferably —$C(O)NR^d$—, —$C(O)O$—, or a five-membered heteroaryl having two heteroatoms selected from N, O, such as oxazole, thiazole, imidazole.

In preferred embodiments $L_1$ is —$(CH_2)_p$—, wherein p is 1, 2 or 3 and $L_2$ is a covalent bond, or (ii) $L_1$ is a covalent bond and $L_2$ is a 5- or 6-membered arylgroup.

In a further embodiment, the side chain containing the oxetane ring is placed at the para position of the benzene ring attached at C4 of the β-lactam.

In one embodiment Z is H and Y is —F in para position.

In another embodiment Z is a polar group A, preferably a polar group A2 and Y is —F in para position.

V is preferably CH(OH), —C(=O)— or —O— and/or wherein W, X, Y and Z independently represent H, halogen, or —OH.

In a specific embodiment S is a group of formula IIIa or IIIb

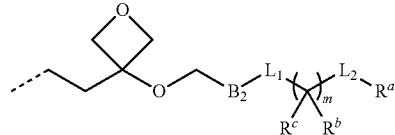

IIIb wherein $B_2$ represents —$C(O)NR^d$—, —$C(O)O$—, aryl or heteroaryl;

$R^a$, $R^d$ represent (i) independently of each other H, (C1-C10) alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_8$, $R_7$, $R_8$, $R_9$, $R_{10}$, $R_{11}$, $R_{12}$, $R_{13}$ are independently of each other H, (C1-C10)alkyl, aryl, or heteroaryl, or combinations thereof such as —(C1-C10)alkyl-aryl, —(C1-C10)alkylcycloalkyl, or one of —(C1-C10)alkyl, cycloalkyl, aryl substituted by at least one polar group A, or (ii) $R^a$ and $R^d$ form together a N-containing 5- or 6-membered heteroaryl or heterocycloalkyl;

$L_1$, $L_2$ represent independently of each other a covalent bond, a 5- or 6-membered arylgroup or a group —$(CH_2)_p$—, wherein p is 1, 2 or 3;

$R^b$, $R^c$ represent (i) independently of each other H, (C1-C10) alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or combinations thereof such as —(C1-C10)alkyl-aryl, —(C1-C10)alkylcycloalkyl, or one of —(C1-C10)alkyl, cycloalkyl, aryl substituted by at least one polar group A, or (ii) $R^b$ and $R^c$ form together a (C3-C6)cycloalkyl or (C3-6)heterocycloalkyl, m is 0, 1 or 2;

with the proviso that at least one of groups $R^a$, $R^b$, $R^c$, $R^d$ is a polar group A.

$B_2$ represents preferably —$C(O)NR^d$—, —$C(O)O$—, or a five-membered heteroaryl having two heteroatoms selected from N, O, such as oxazole, thiazole, imidazole.

The at least one of groups $R^a$, $R^b$, $R^c$, $R^d$ is preferably a polar group A1.

In preferred embodiments $L_1$ is —$(CH_2)_p$—, wherein p is 1, 2 or 3 and $L_2$ is a covalent bond, or (ii) $L_1$ is a covalent bond and $L_2$ is a 5- or 6-membered arylgroup.

In a further specific embodiment S is a group of formula IVa, IVb, IVc or formula Va, Vb, Vc

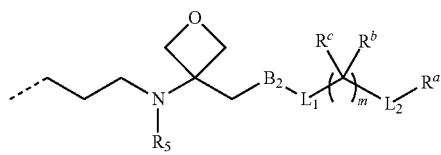

IIIa

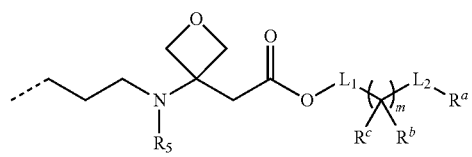

IVa

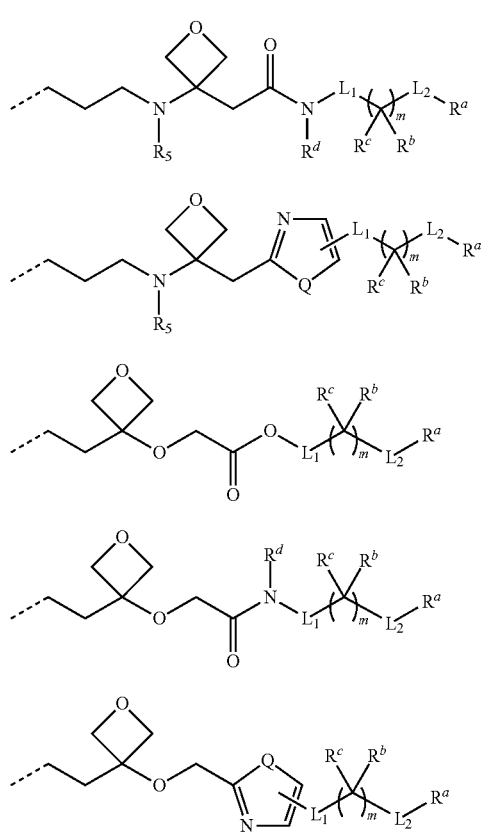

wherein
Q is —O—, —NR$_5$—, —S—,
L$_1$, L$_2$ represent independently of each other a covalent bond, a 5- or 6-membered arylgroup or a group —(CH$_2$)$_p$—, wherein p is 1, 2 or 3;

R$_5$ is H, (C1-C6)alkyl, benzyl or aryl;
m is 0, 1 or 2;
R$^a$, R$^d$ represent independently of each other H, (C1-C10)alkyl, cycloalkyl, aryl, or a polar group A selected from halogen, epoxy, —COR$_6$, —COOR$_7$, —NR$_8$R$_9$, —N$^+$R$_8$R$_9$R$_{10}$, —OR$_{11}$, —CONR$_{12}$N$_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein R$_6$, R$_7$, R$_8$, R$_9$, R$_{10}$, R$_{11}$, R$_{12}$, R$_{13}$ are independently of each other H, (C1-C10)alkyl, aryl, or heteroaryl, or combinations thereof such as —(C1-C10)alkylaryl, —(C1-C10)alkyl-cycloalkyl, or one of —(C1-C10)alkyl, cycloalkyl, aryl substituted by at least one polar group A, or R$^a$ and R$^d$ form together a N-containing 5- or 6-membered heteroaryl or heterocycloalkyl;

R$^b$, R$^c$ represent (i) independently of each other H, (C1-C10)alkyl, cycloalkyl, aryl, or a polar group A selected from halogen, epoxy, —COR$_6$, —COOR$_7$, —NR$_8$R$_9$, —N$^+$R$_8$R$_9$R$_{10}$, —OR$_{11}$, —CONR$_{12}$N$_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein R$_6$, R$_7$, R$_8$, R$_9$, R$_{10}$, R$_{11}$, R$_{12}$, R$_{13}$ are independently of each other H, (C1-C10)alkyl, aryl, or heteroaryl, or combinations thereof such as —(C1-C10)alkyl-aryl, —(C1-C10)alkyl-cycloalkyl, or one of —(C1-C10)alkyl, cycloalkyl, aryl substituted by at least one polar group A, or (ii) R$^b$ and R$^c$ form together a (C3-C6)cycloalkyl or (C3-6)heterocycloalkyl;

with the proviso that at least one of groups R$^a$, R$^b$, R$^c$, R$^d$ is a polar group A.

The at least one of groups R$^a$, R$^b$, R$^c$, R$^d$ is preferably a polar group A1.

In a specific embodiment the present invention relates to compounds of the present invention having formula VIa, VIb, VIc or formula VIIIa, VIIb, VIIc or a pharmaceutically acceptable salt thereof,

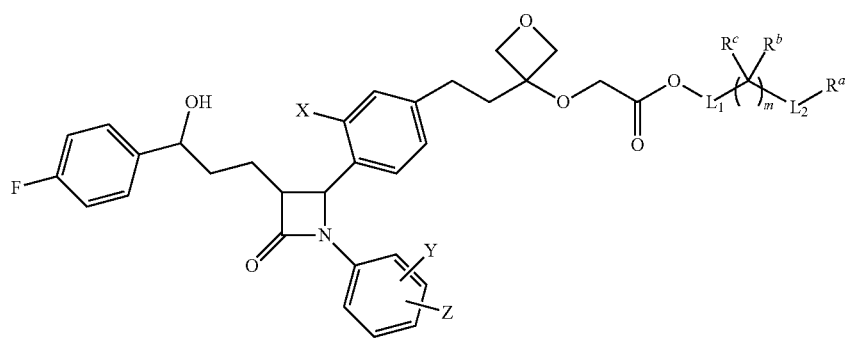

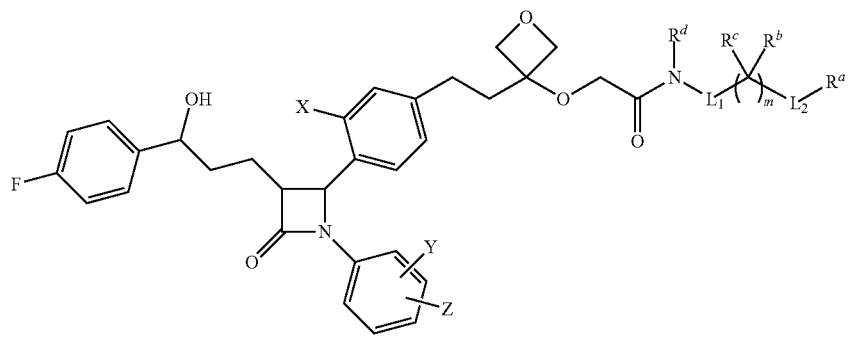

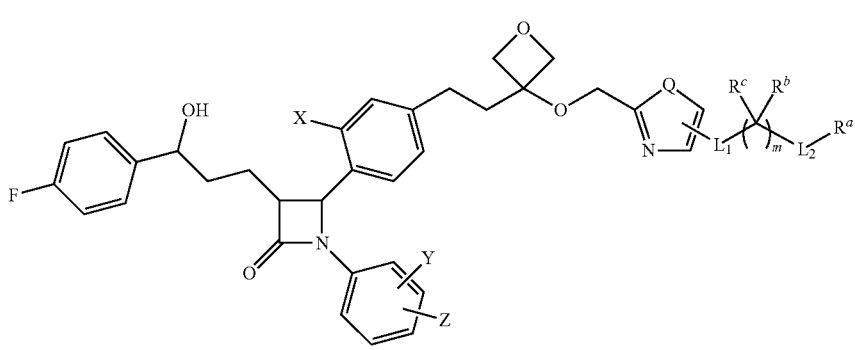

VIc

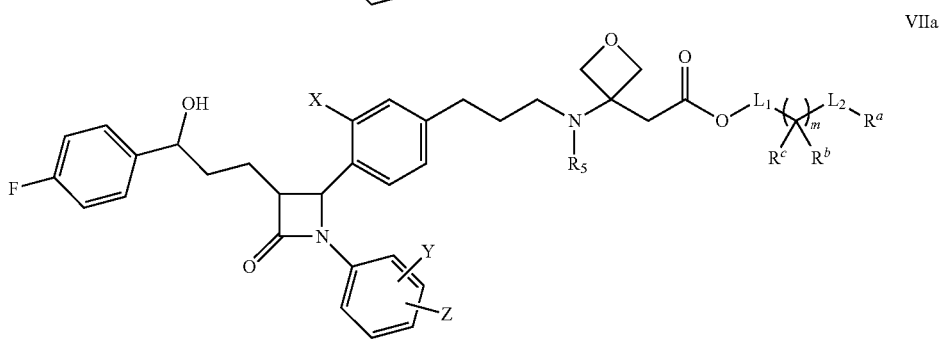

VIIa

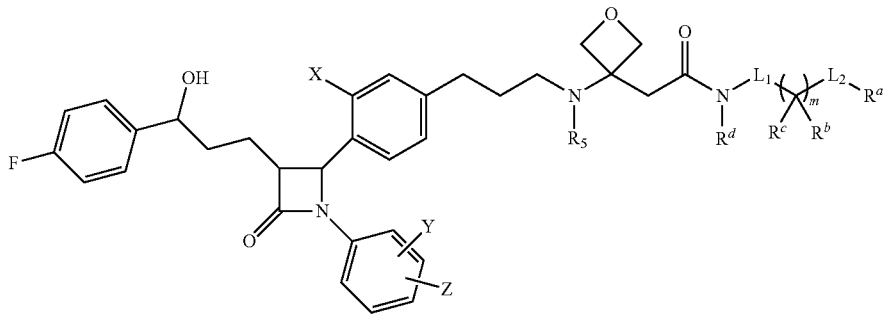

VIIb

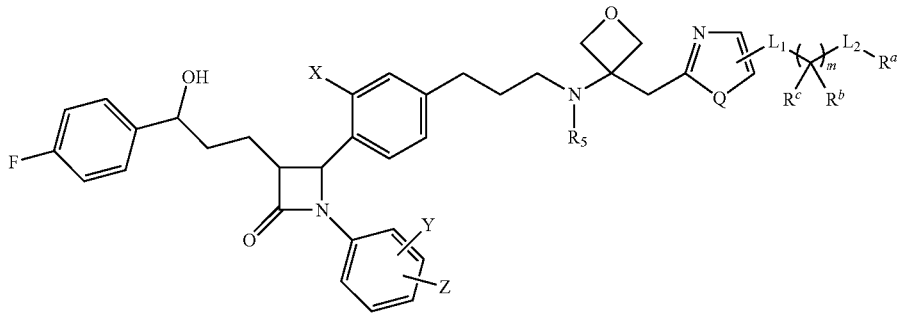

VIIc wherein

X, Y are, independently of each other, H, OH or F;

Z represents H, —(C1-C10)alkyl, —(C1-C10)alkenyl, —(C1-C10)alkynyl, aryl, or a polar group A selected from halogen, epoxy, —COR$_6$, —COOR$_7$, —NR$_8$R$_9$, —N$^+$R$_8$R$_9$R$_{10}$, —OR$_{11}$, —CONR$_{12}$N$_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein R$_6$, R$_7$, R$_8$, R$_9$, R$_{10}$, R$_{11}$, R$_{12}$, R$_{13}$ are independently of each other H, (C1-C10)alkyl, aryl, or heteroaryl, or combinations thereof such as —(C1-C10)alkylaryl, —(C1-C10)alkenyl-aryl, —(C1-C10)alkynyl-aryl, or one of —(C1-C10)alkyl, —(C1-C10)alkenyl, —(C1-C10)alkynyl, aryl substituted by at least one polar group A;

Q is —O—, —NR$_5$—, —S—, m is 0, 1 or 2;

L$_1$, L$_2$ represent independently of each other a covalent bond, a 5- or 6-membered arylgroup or a group —(CH$_2$)$_p$—, wherein p is 1, 2 or 3;

R$_5$ is H, (C1-C6)alkyl, benzyl or aryl;

R$^a$, R$^d$ represent independently of each other (i) H, (C1-C10) alkyl, cycloalkyl, aryl, or a polar group A selected from halogen, epoxy, —COR$_6$, —COOR$_7$, —NR$_8$R$_9$, —N$^+$R$_8$R$_9$R$_{10}$, —OR$_{11}$, —CONR$_{12}$N$_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or combinations thereof such as —(C1-C10)alkyl-aryl, —(C1-C10)alkyl-cycloalkyl, or one of —(C1-C10)alkyl, cycloalkyl, aryl substituted by at least one polar group A, or (ii) $R^a$ and $R^d$ form together a N-containing 5- or 6-membered heteroaryl or heterocycloalkyl;

$R^b$, $R^c$ represent (i) independently of each other H, (C1-C10) alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R^{13}$ are independently of each other H, (C1-C10)alkyl, aryl, or heteroaryl, or combinations thereof such as —(C1-C10)alkyl-aryl, —(C1-C10)alkyl-cycloalkyl, or one of —(C1-C10)alkyl, cycloalkyl, aryl substituted by at least one polar group A, or (ii) $R^b$ and $R^c$ form together a (C3-C6)cycloalkyl or (C3-6)heterocycloalkyl;

with the proviso that at least one of groups $R^a$, $R^b$, $R^c$, $R^d$ is a polar group A.

In preferred embodiments $L_1$ is —$(CH_2)_p$—, wherein p is 1, 2 or 3 and $L_2$ is a covalent bond, or (ii) $L_1$ is a covalent bond and $L_2$ is a 5- or 6-membered arylgroup.

In one embodiment Z is H and Y is preferably —F in para position.

In another embodiment the at least one of groups $R^a$, $R^b$, $R^c$, $R^d$ is a polar group A1.

In yet another embodiment Z is a polar group A, preferably a polar group A2, and Y is preferably —H or —F.

In yet further preferred embodiments the invention is directed towards compounds of formula VIIIa or VIIIb wherein X, Y are independently of each other, H, OH or F;

Z represents H, —(C1-C10)alkyl, —(C1-C10)alkenyl, —(C1-C10)alkynyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl or heteroaryl, or combinations thereof such as —(C1-C10)alkyl-aryl, —(C1-C10)alkenyl-aryl, —(C1-C10)alkynyl-aryl, or one of —(C1-C10)alkyl, —(C1-C10)alkenyl, —(C1-C10)alkynyl, aryl substituted by at least one polar group A;

$R^b$, $R^c$ represent independently of each other H, (C1-C10) alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}N_{13}$, phosphate groups, phosphonate groups, sulfonate groups, sulfonyl groups, sulfonamides, polyhydroxy, a 4- to 7-membered heteroaryl or heterocycloalkyl having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or combinations thereof such as —(C1-C10)alkylaryl, —(C1-C10)alkyl-cycloalkyl, or one of —(C1-C10)alkyl, cycloalkyl, aryl substituted by at least one polar group A, with the proviso that at least one of groups $R^b$ and $R^c$ is a polar group A, $L_1$, $L_2$ represent independently of each other a covalent bond or —$(CH_2)_p$—, wherein p is 1, 2 or 3, and $R_5$ is H or (C1-C6)alkyl, benzyl or aryl.

Preferably, the substituents at the 3- and 4-position of the β-lactam ring are in trans configuration to each other.

Preferably, X is ortho to the β-lactam ring;

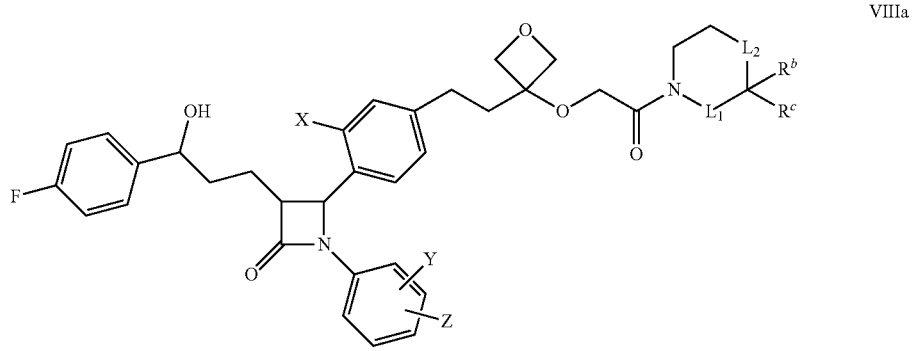

VIIIa

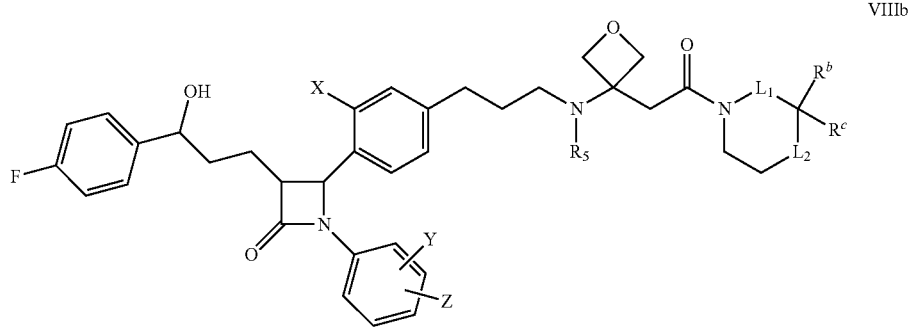

VIIIb

Preferably, Y is meta to the β-lactam and Z is para, or Y is para and Z is meta.

In one embodiment Z is H and Y is preferably —F in para position. In another embodiment Z is a polar group A, preferably a polar group A2 and Y is preferably —H or —F.

In a further aspect the present invention relates to methods of preparation of the compounds of the invention.

In one embodiment the precursor in the synthesis of the compounds of the invention was synthesized according the synthetic route shown in scheme 1.

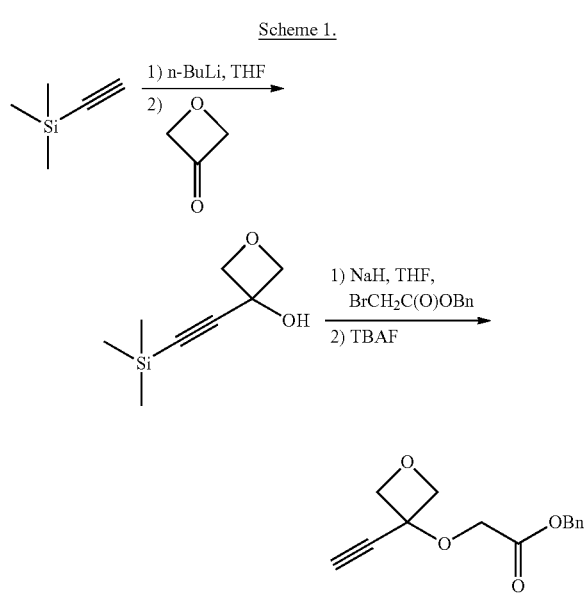

In another embodiment the precursor in the synthesis of the compounds of the invention was synthesized according the synthetic route shown in scheme 2.

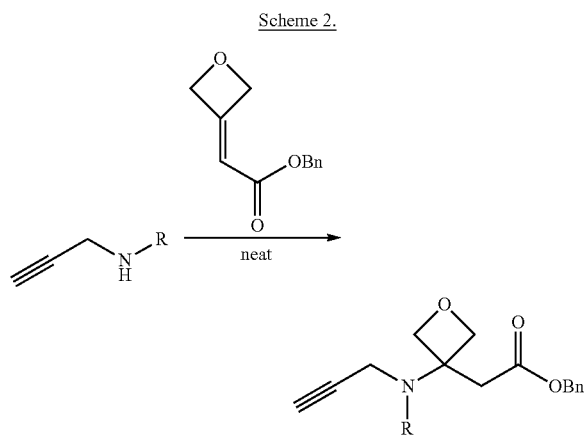

In another embodiment the compounds of the invention were synthesized by coupling a beta-lactam derivative with the precursors described in route A or B as described in Scheme 3, where X is a suitable group for Pd-catalysed C—C bond formation between an aryl group and a terminal alkyne moiety ((i) Sonogashira coupling; (ii) Pd/C, H₂, EtOH).

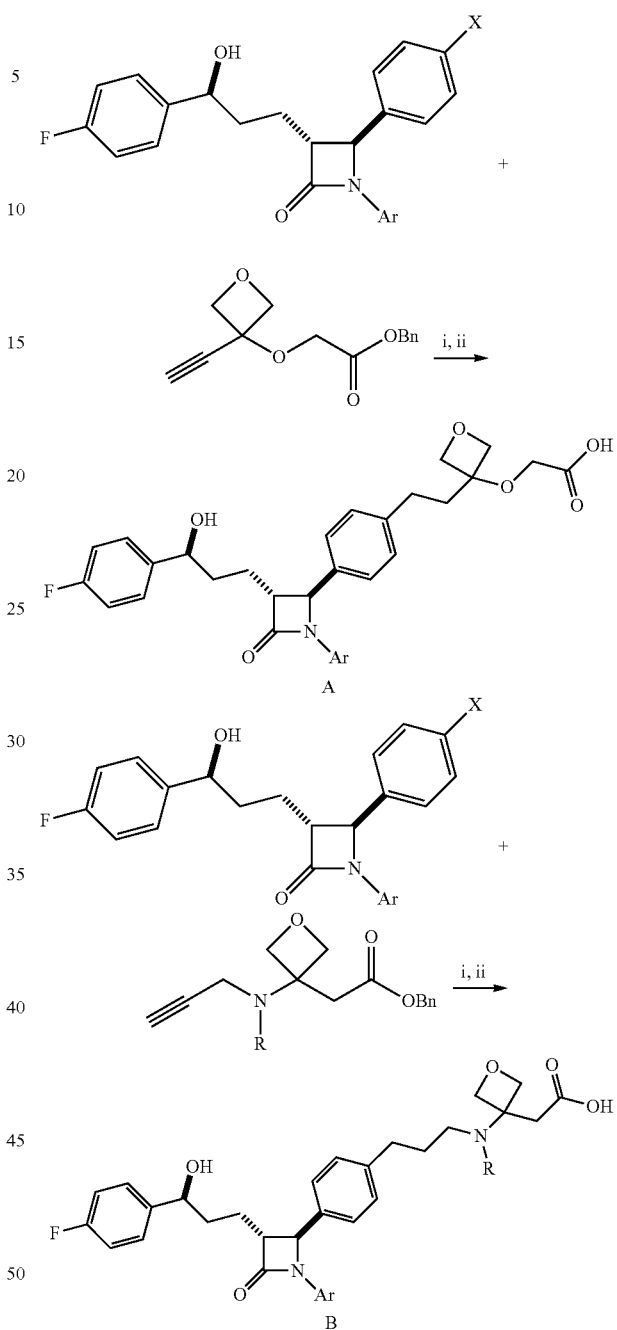

The final products in scheme 3 were used to synthesize other derivatives by modification of the carboxylic acid moiety. Alternatively, derivatization of the carboxylic acid may be performed before the Sonogashira coupling (i).

It has further been shown that the compounds of the invention display the desired pharmacological activity by evaluation of their potency in vivo (in mice and hamsters). The bioavailability of the compounds of the present invention has been determined by unidirectional Caco2 Permeability measurement.

Thus, the compounds of the invention and their pharmaceutically acceptable acid addition salts, exhibit pharmacological activity and are, therefore, useful as pharmaceuticals. The compounds of the invention have been shown to effectively inhibit cholesterol absorption and are therefore useful in the treatment and/or prevention of atherosclerosis and of the reduction of cholesterol levels.

Thus in yet a further aspect, the present invention is directed to a method of treatment and/or prevention of atherosclerosis, of the reduction of cholesterol levels and of treating or preventing a vascular condition, comprising administering to a mammal in need of such treatment an effective amount of a compound of the present invention.

The novel compounds of the present invention can be used, for example, in the form of pharmaceutical compositions containing a therapeutically effective amount of the active ingredient, if appropriate together with inorganic or organic, solid or liquid, pharmaceutically acceptable carriers suitable for enteral, e.g. oral, or parenteral administration. Accordingly, tablets or gelatin capsules are used that contain the active ingredient together with diluents, typically lactose, dextrose, saccharose, mannitol, sorbitol, cellulose and/or lubricants, e.g. diatomaceous earth, talcum, stearic acid or salts thereof, such as magnesium stearate or calcium stearate, and/or polyethylene glycol. Tablets may also contain binders, typically magnesium aluminium silicate, starches, typically corn starch, wheat starch, rice starch or arrow root starch, gelatin, tragacanth, methylcellulose, sodium carboxymethylcellulose and/or polyvinylpyrrolidone, and, if desired, disintegrators, typically starches, agar, alginic acid or a salt thereof, e.g. sodium alginate, and/or effervescent mixtures, or absorbents, colourants, flavourings and sweeteners.

Thus in another aspect, the invention relates to a pharmaceutical composition comprising a compound of the present invention (and optionally other therapeutically effective agents), and a pharmaceutically acceptable carrier for the treatment or prevention of artheriosclerosis or for the reduction of cholesterol levels.

The terms "effective amount" and "therapeutically effective amount" mean that amount of a compound of the present invention (and optionally other therapeutically effective agents), that will elicit a biological or medical response of a tissue, system, animal or mammal, which includes alleviation of the symptoms of the condition or disease being treated and the prevention, slowing or halting of progression of one or more conditions, for example atherosclerosis, hypercholesterolemia.

The pharmaceutical compositions so obtained which, if desired, contain further pharmacologically active substances, are prepared in a manner known per se by conventional mixing, granulating, sugar-coating, solution or lyophilising methods and contain from about 0.1% to 100%, preferably from about 1% to about 50%, lyophilisate to about 100%, of active ingredient.

The compounds, compositions and treatments of the present invention can be administered by any suitable means which produce contact of these compounds with the site of action in the body, for example in the plasma, liver or small intestine of a mammal or human. Thus the novel compounds of the present invention may also be used in the form of compositions for parenteral, oral, transdermal administration or infusion solutions. Such solutions are preferably isotonic aqueous solutions or suspension which, e.g. in the case of lyophilised compositions that contain the active ingredient by itself or together with a carrier, such as mannitol, can be prepared before use. The pharmaceutical compositions can be sterilised and/or can contain excipients, typically preservatives, stabilisers, wetting agents and/or emulsifiers, solubilisers, salts for regulating the osmotic pressure and/or buffers.

In yet a further aspect, the invention relates to a kit comprising an effective amount of a compound of the present invention in a pharmaceutically acceptable carrier (and optionally an effective amount of another therapeutically effective agent), optionally in separate compartments.

The following non-limiting Examples illustrate the above-described invention in more detail.

EXAMPLES

Materials and Methods

Reactions in anhydrous solvents were all performed using oven dried glassware under an atmosphere of $N_2$. Reagent grade solvents were all purchased from chemical companies and used without prior purification. For chromatographic purification, technical grade solvents were distillated prior to use. TLC was performed using Machery-Nagel Alugram Sil G/UV$_{254}$ TLC plates and visualized with ultraviolet light at 254 nm and CAM, p-anisaldehyde or $KMnO_4$ staining. Chromatographic purification of products was accomplished by flash chromatography on silica gel 60 (230-400 mesh, 0.04-0.063 mm) from Merck at rt and 0.3-0.5 mbar air pressure or with a Armen Spotflash Automated Purification System and commercial prepacked silica gel cartridges; fractions containing product were pooled, the solvents were evaporated under reduced pressure and the residue was dried under high vacuum to give the product. NMR spectra were recorded on a Varian Mercury 300 MHz apparatus operating at 300 MHz and 75 MHz for $^1$H and $^{13}$C, respectively, and chemical shifts ($\delta$) were referenced to the internal solvent signals. Melting points were measured on a Büchi 510 apparatus in open capillaries and all melting points are uncorrected. IR-Spectra were recorded in $CHCl_3$ on a Perkin Elmer Spectrum RX I FT-IR apparatus (thin films on NaCl plates) and are reported as absorption maxima in $cm^{-1}$ (data not submitted). High resolution matrix-assisted laser desorption ionization mass spectrometry (MALDI-MS) and electrospray ionization (ESI-MS) were performed by the mass spectrometry service of the LOC at the ETH, Zürich and were recorded in positive ion mode. Analytical LC/MS was performed on a Dionex 3000 UPtimate System. The flow rate was 1 mL/min. Column: Agilent Technologies Eclipse Plus C18 (RP-18, 3.5 μm, 3.0×30 mm). Solvent A: $CH_3CN$, Solvent B: 0.1% TFA in $H_2O$. All separations were performed at 35° C.

Example 1

2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetic acid $t_R$=2.99 min, [M+H]+=552.3;

(a) Synthesis of benzyl 2-(3-ethynyloxetan-3-yloxy)acetate

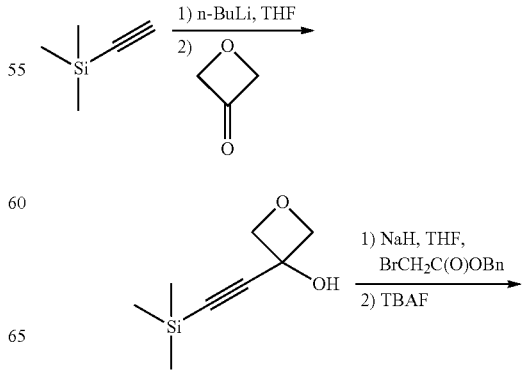

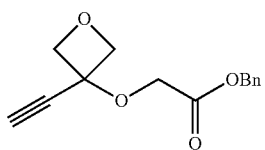

To a solution of TMS-acetylene (5.12 mL) in THF (20 mL) at −78° C. was added n-BuLi (1.6M in hexanes, 21.1 mL). The reaction was stirred at −78° C. for 20 min and a solution of oxetane-3-one (2 g) in THF (2 mL) was added. The reaction mixture was stirred at −78° C. for an additional 30 min and an aliquot was evaporated (white solid). The reaction mixture was evaporated to give a foam that was used in the next reactions.

To a suspension of sodium hydride (60% suspension, 117 mg) in DMF (2 mL) was added the above alcohol (400 mg, in 1.5 mL DMF). The reaction mixture was stirred at RT for 2 h and ethyl bromoacetate (0.52 mL) was added. The reaction mixture was stirred at RT for 1 h, followed by addition of sat. aq. NH$_4$Cl and extraction with ethyl acetate. After evaporation the residue was purified by flash chromatography to afford a mixture of TMS-protected (200 mg) and TMS-deprotected (113 mg) alkynes as colourless oil. The former could be transformed into the later by treatment of the mixture with TBAF in THF (typically 80% yield).

(b) Synthesis of 2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetic acid

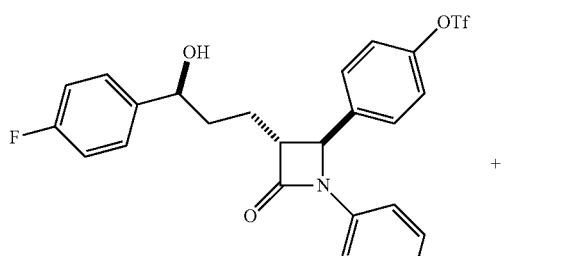

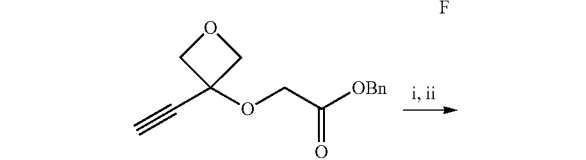

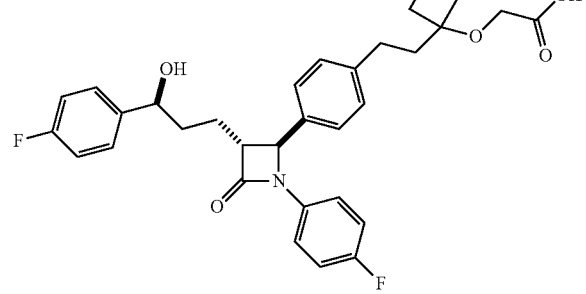

Pd(PPh$_3$)$_4$ (0.15 eq.), CuI (0.30 eq.), TBAI (2.5 eq.), triflate (0.66 g) and benzyl 2-(3-ethynyloxetan-3-yloxy)acetate (0.44 g, 1.5 eq.) were placed in a flask and dissolved in acetonitrile. Triethylamine (6 eq.) was added under N$_2$ and the reaction mixture was stirred at 30° C. for 16 h.

The reaction was quenched by addition of sat. aq. NH$_4$Cl and extracted with EtOAc. The combined organic extracts were combined and evaporated. The residue was dry-loaded on FC to give the coupling product as a colourless oil (0.61 g). The oil was placed in a flask with Pd/C (10%, 100 mg) and EtOH (10 mL) and atmosphere was replaced with H$_2$. Stirring under H$_2$ atmosphere (1 atm) for 3 h, followed by filtration through a pad of celite and evaporation of the solvent afforded 2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetic acid as a white foam (0.49 g).

Example 2

Synthesis of 2-(3-((3-(4-((2S,3R)-1-(4-fluorophenyl)-3-((S)-3-(4-fluorophenyl)-3-hydroxypropyl)-4-oxoazetidin-2-yl)phenyl)propyl)(methyl)amino)oxetan-3-yl)acetic acid (a) Synthesis of benzyl 2-(3-(methyl (prop-2-ynyl)amino)oxetan-3-yl)acetate

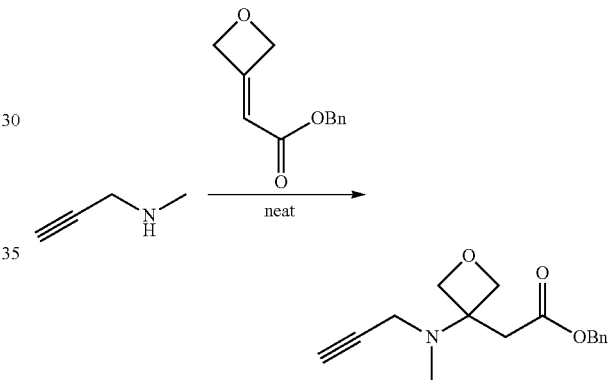

A mixture of N-methyl-propargylamine (0.27 g) and benzyl 2-(oxetan-3-ylidene)acetate (0.41 g) was stirred neat at RT for 12 h. The excess amine was removed by evaporation to give benzyl 2-(3-(methyl(prop-2-ynyl)amino)oxetan-3-yl)acetate quantitatively (0.54 g).

(b) Synthesis of 2-(3-((3-(4-((2S,3R)-1-(4-fluorophenyl)-3-((S)-3-(4-fluorophenyl)-3-hydroxypropyl)-4-oxoazetidin-2-yl)phenyl)propyl)(methyl)amino)oxetan-3-yl)acetic acid

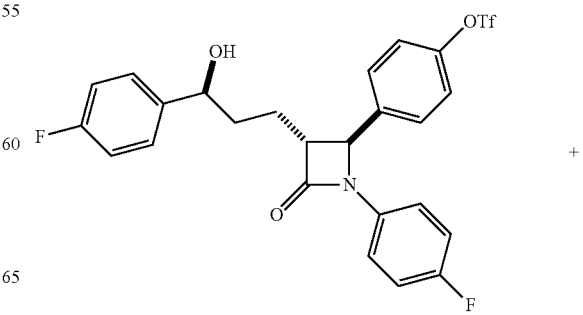

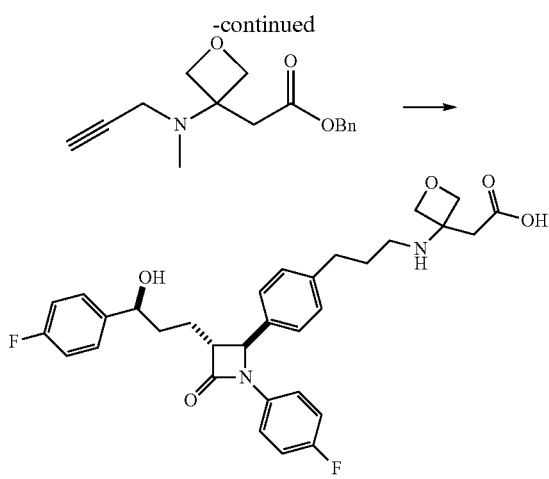

The reaction between the above triflate (0.5 g) and benzyl 2-(3-(methyl(prop-2-ynyl)amino)oxetan-3-yl)acetate (1.5 eq.) obtained in step (a) under the coupling conditions described in Example 1 afforded, after Sonogashira coupling and hydrogenation, 2-(3-((3-(4-((2S,3R)-1-(4-fluorophenyl)-3-((S)-3-(4-fluorophenyl)-3-hydroxypropyl)-4-oxoazetidin-2-yl)phenyl)propyl)(methyl)amino)oxetan-3-yl)acetic acid as a white foam (0.32 g).

Example 3

(R)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-3-phenylpropanoic acid $t_R$=3.43 min, [M+H]+=700.0;

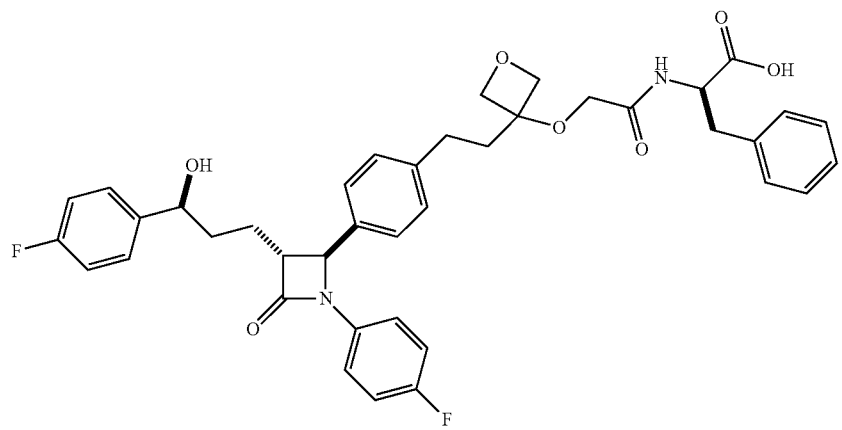 [SMILES: O=C(COC1(CCc2ccc([C@@H]3[C@@H](CC[C@H](O)c4ccc(F)cc4)C(=O)N3c3ccc(F)cc3)cc2)COC1)N[C@H](Cc1ccccc1)C(=O)O]

Example 4

2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-3-(4-hydroxyphenyl)-2-methylpropanoic acid $t_R$=3.02 min, [M−4H+Na]+=747.0;

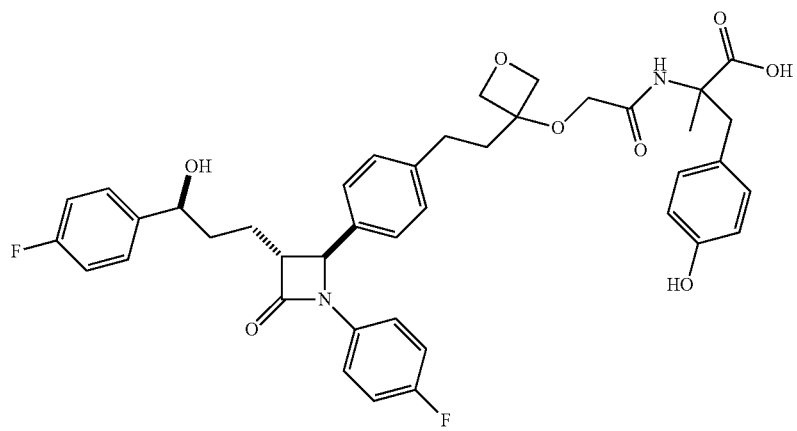 [SMILES: CC(Cc1ccc(O)cc1)(NC(=O)COC1(CCc2ccc([C@@H]3[C@@H](CC[C@H](O)c4ccc(F)cc4)C(=O)N3c3ccc(F)cc3)cc2)COC1)C(=O)O]

Example 5
3-cyclohexyl-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)propanoic acid
$t_R$=3.60 min, [M+H$_2$O]+=721.6;
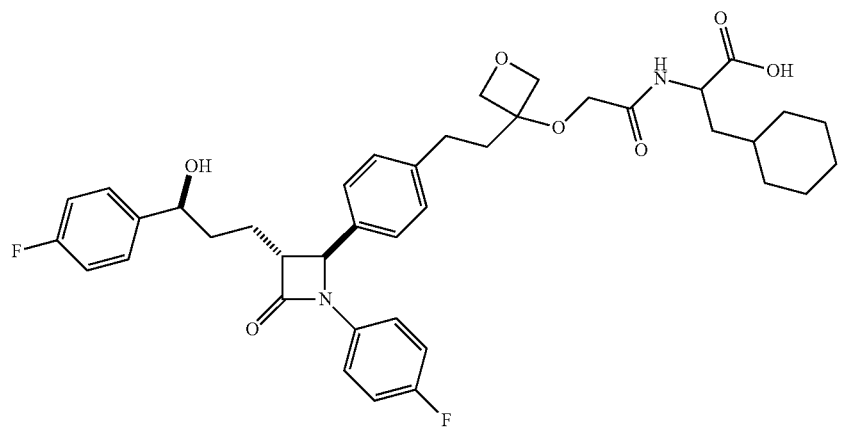 [SMILES: O=C(COC1(CCc2ccc([C@@H]3[C@@H](CC[C@H](O)c4ccc(F)cc4)C(=O)N3c3ccc(F)cc3)cc2)COC1)NC(CC1CCCCC1)C(=O)O]
Example 6
(R)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-2-phenylacetic acid
$t_R$=3.49 min, [M+H]$^+$=685.0;
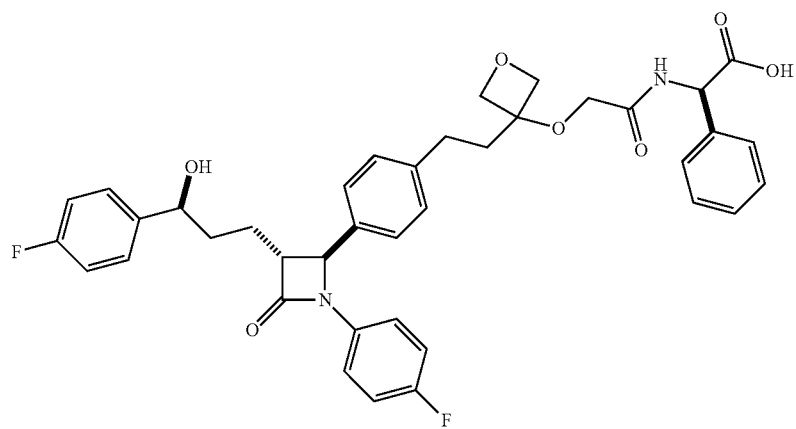 [SMILES: O=C(COC1(CCc2ccc([C@@H]3[C@@H](CC[C@H](O)c4ccc(F)cc4)C(=O)N3c3ccc(F)cc3)cc2)COC1)N[C@@H](C(=O)O)c1ccccc1]

Example 7
(R)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-2-(4-hydroxyphenyl)acetic acid
$t_R$=2.98 min, [M+H]+=701.2;
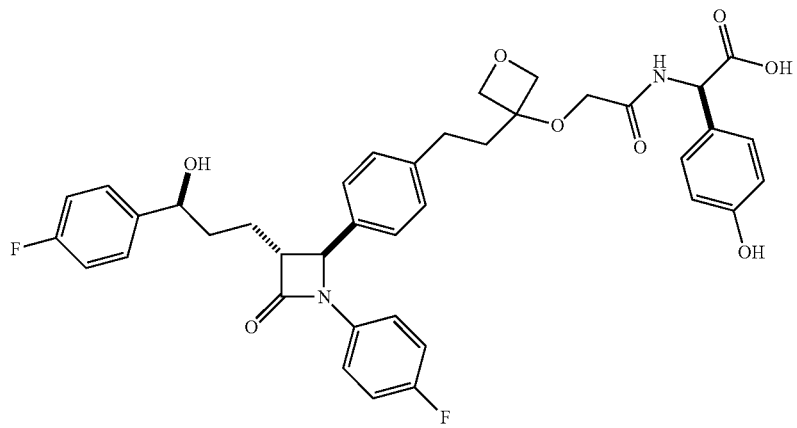 [SMILES: O=C(COC1(CCc2ccc([C@@H]3[C@@H](CC[C@H](O)c4ccc(F)cc4)C(=O)N3c3ccc(F)cc3)cc2)COC1)N[C@@H](C(=O)O)c1ccc(O)cc1]
Example 8
1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetyl)piperidine-3-carboxylic acid
$t_R$=3.15 min, [M+H]+=663.2;
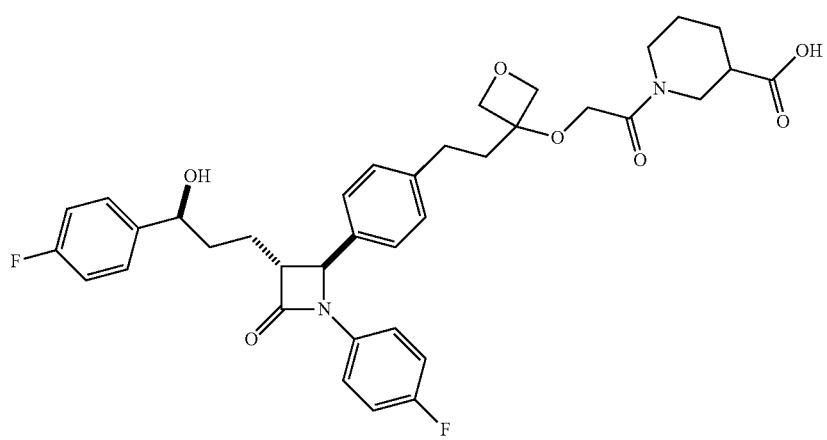 [SMILES: O=C(O)C1CCCN(C(=O)COC2(CCc3ccc([C@@H]4[C@@H](CC[C@H](O)c5ccc(F)cc5)C(=O)N4c4ccc(F)cc4)cc3)COC2)C1]

Example 9
1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetyl)piperidine-4-carboxylic acid
$t_R$=2.89 min, [M+H]+=663.2;
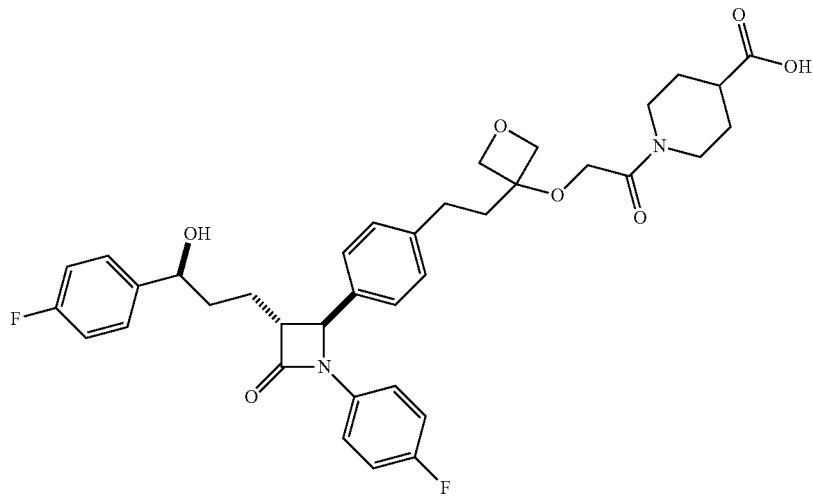 [SMILES: O=C(O)C1CCN(C(=O)COC2(CCc3ccc([C@@H]4[C@@H](CC[C@H](O)c5ccc(F)cc5)C(=O)N4c4ccc(F)cc4)cc3)COC2)CC1]
Example 10
3-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-4-methylpentanoic acid
$t_R$=3.25 min, [M−2H+K]+=701.0;
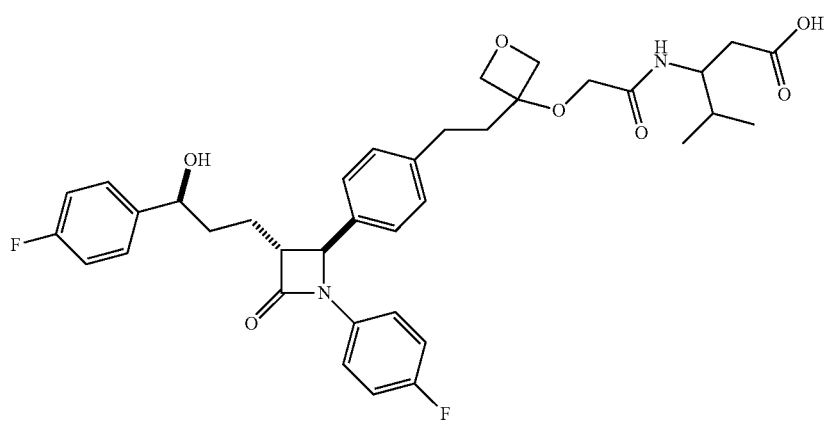 [SMILES: CC(C)C(CC(=O)O)NC(=O)COC1(CCc2ccc([C@@H]3[C@@H](CC[C@H](O)c4ccc(F)cc4)C(=O)N3c3ccc(F)cc3)cc2)COC1]

Example 11
2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)-N-methyl-N-(2,3,4,5,6-pentahydroxyhexyl)acetamide
$t_R$=2.71 min, [M+H]+=729.0;
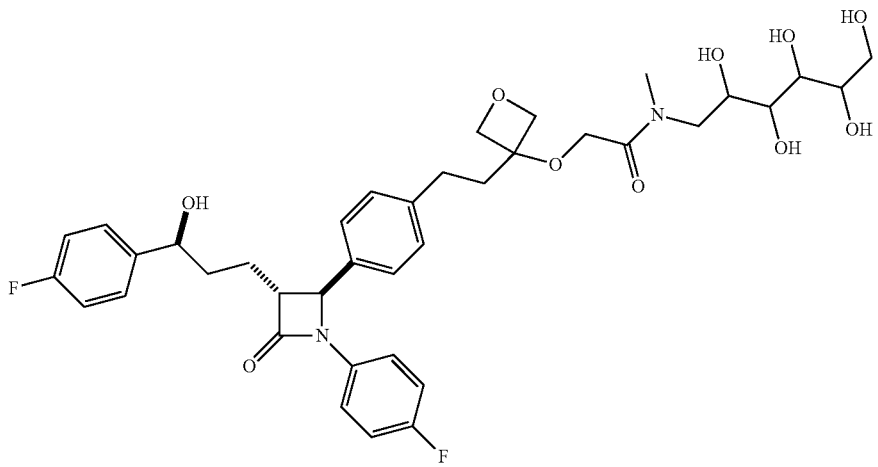 [SMILES: CN(CC(O)C(O)C(O)C(O)CO)C(=O)COC1(CCc2ccc([C@@H]3[C@@H](CC[C@H](O)c4ccc(F)cc4)C(=O)N3c3ccc(F)cc3)cc2)COC1]
Example 12
N-(2-(dimethylamino)ethyl)-2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamide
$t_R$=2.23 min, [M+H]+=622.1;
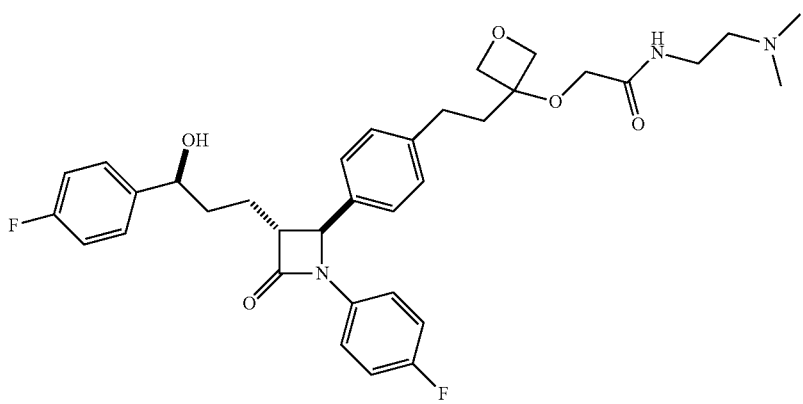 [SMILES: CN(C)CCNC(=O)COC1(CCc2ccc([C@@H]3[C@@H](CC[C@H](O)c4ccc(F)cc4)C(=O)N3c3ccc(F)cc3)cc2)COC1]

Example 13
2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-N,N,N-trimethylethanaminium iodide
$t_R$=2.21 min, [M]-1-=636.1;
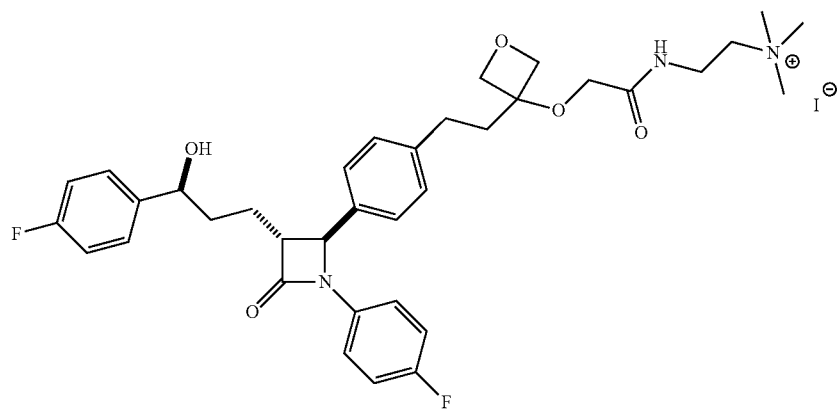 [SMILES: C[N+](C)(C)CCNC(=O)COC1(CCc2ccc([C@@H]3[C@@H](CC[C@H](O)c4ccc(F)cc4)C(=O)N3c3ccc(F)cc3)cc2)COC1 ; [I-]]
Example 14
2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)-N-(2-morpholinoethyl)acetamide
$t_R$=2.28 min, [M+H]+=664.1;
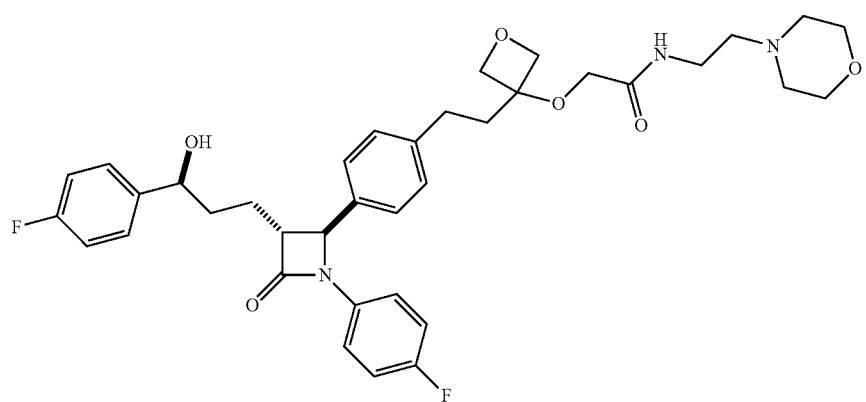 [SMILES: O=C(COC1(CCc2ccc([C@@H]3[C@@H](CC[C@H](O)c4ccc(F)cc4)C(=O)N3c3ccc(F)cc3)cc2)COC1)NCCN1CCOCC1]

Example 15
4-(2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)ethyl)-4-methylmorpholin-4-ium iodide
$t_R$=2.26 min, [M+H]+=678.1;
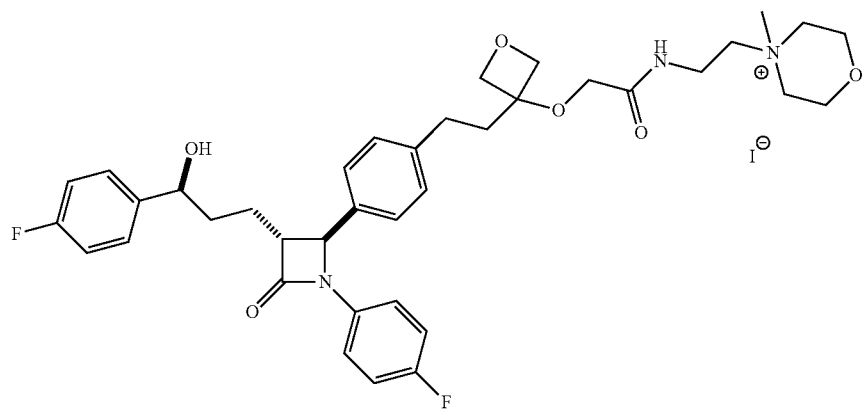 [SMILES: C[N+]1(CCNC(=O)COC2(CCc3ccc([C@@H]4[C@@H](CC[C@H](O)c5ccc(F)cc5)C(=O)N4c4ccc(F)cc4)cc3)COC2)CCOCC1 ; [I-]]
Example 16
3-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)benzoic acid
$t_R$=2.95 min, [M+NH$_4$]+=689.1;
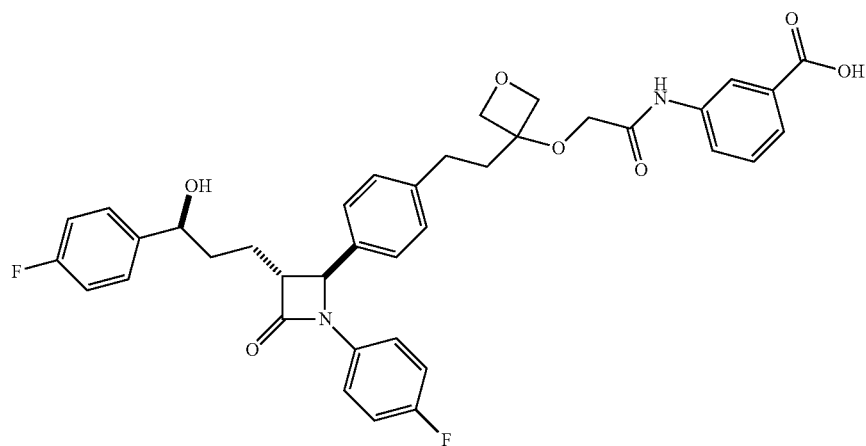 [SMILES: O=C(COC1(CCc2ccc([C@@H]3[C@@H](CC[C@H](O)c4ccc(F)cc4)C(=O)N3c3ccc(F)cc3)cc2)COC1)Nc1cccc(C(=O)O)c1]

Example 17
4-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)benzoic acid
$t_R$=2.92 min, [M+NH$_4$]+=689.1;
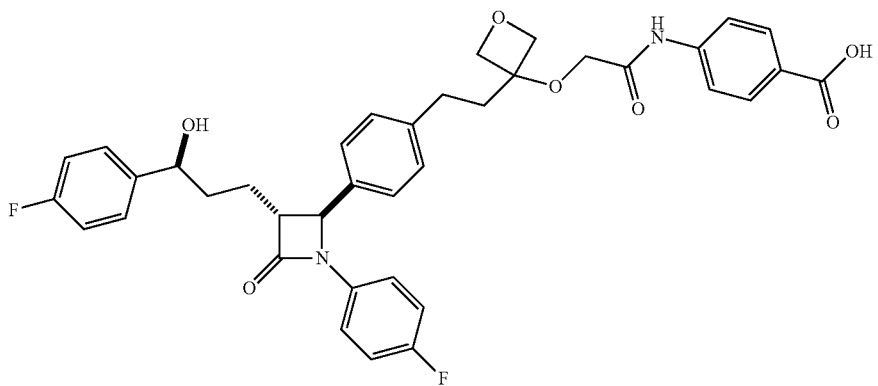 [SMILES: O=C(COC1(CCc2ccc([C@@H]3[C@@H](CC[C@H](O)c4ccc(F)cc4)C(=O)N3c3ccc(F)cc3)cc2)COC1)Nc1ccc(C(=O)O)cc1]
Example 18
2-((3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)methyl)oxazole-4-carboxylic acid
$t_R$=3.35 min, [M−H+H$_2$O]+=631.8;
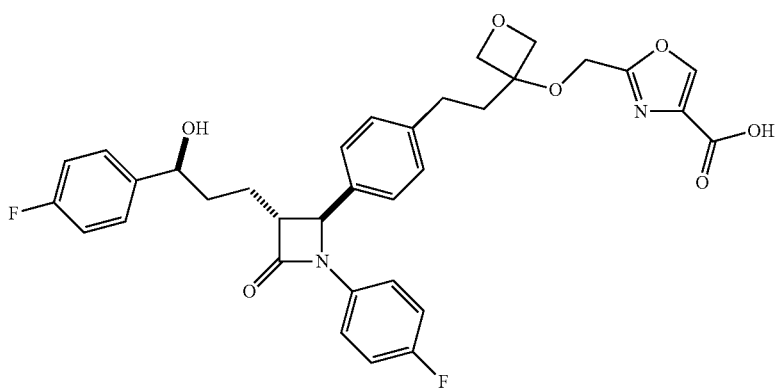 [SMILES: O=C(O)c1coc(COC2(CCc3ccc([C@@H]4[C@@H](CC[C@H](O)c5ccc(F)cc5)C(=O)N4c4ccc(F)cc4)cc3)COC2)n1]

Example 19
(R)-1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetyl)pyrrolidine-2-carboxylic acid
$t_R$=3.12 min, [M+H]+=649.1;
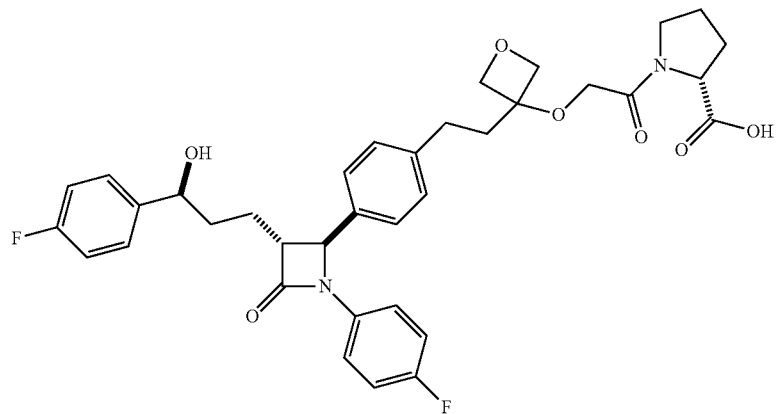
Example 20
(S)-1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetyl)pyrrolidine-2-carboxylic acid
$t_R$=2.96 min, [M+H]+=649.1;
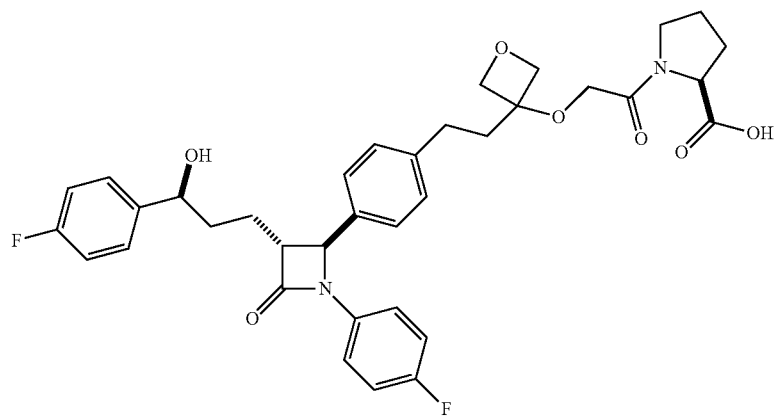 [SMILES: O=C(O)[C@@H]1CCCN1C(=O)COC1(CCc2ccc([C@@H]3[C@@H](CC[C@H](O)c4ccc(F)cc4)C(=O)N3c3ccc(F)cc3)cc2)COC1]

Example 21
(3R,4S)-4-(4-(2-(3-(2-((S)-2-(1H-tetrazol-5-fluorophenyl)-3-((S)-3-(4-fluorophenyl)-3-hydroxypropyl)azetidin-2-one
$t_R$=2.97 min, [M+H]+=673.1;
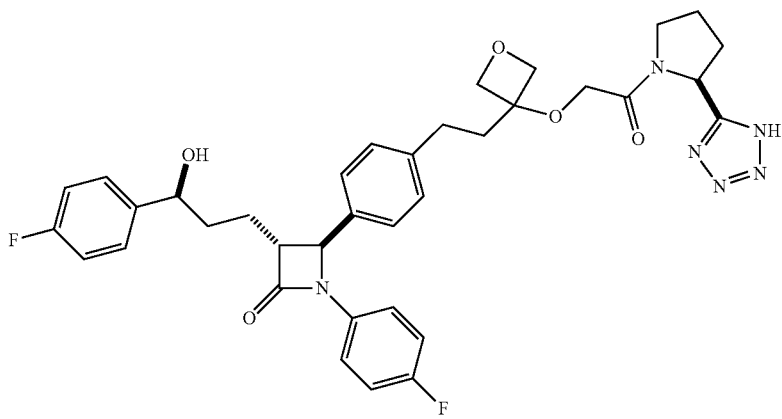 [SMILES: O=C(COC1(CCc2ccc([C@@H]3[C@@H](CC[C@H](O)c4ccc(F)cc4)C(=O)N3c3ccc(F)cc3)cc2)COC1)N1CCC[C@H]1c1nnn[nH]1]
Example 22
(R)-1-(2-(3-(4-(((2S,3R)-1-(4-fluorophenyl)-3-((S)-3-(4-fluorophenyl)-3-hydroxypropyl)-4-oxoazetidin-2-yl)phenethyl)oxetan-3-yloxy)acetyl)pyrrolidine-2-carboxamide
$t_R$=2.83 min, [M+H]+=647.7;
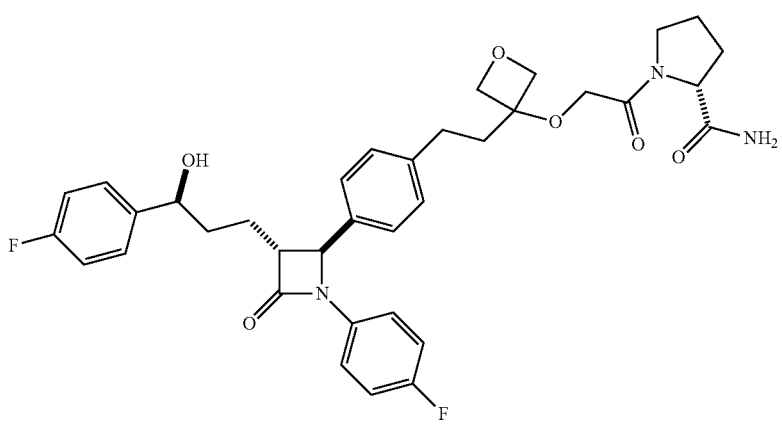 [SMILES: NC(=O)[C@H]1CCCN1C(=O)COC1(CCc2ccc([C@@H]3[C@@H](CC[C@H](O)c4ccc(F)cc4)C(=O)N3c3ccc(F)cc3)cc2)COC1]

Example 23
1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetyl)piperidine-2-carboxylic acid
$t_R$=3.10 min, [M+H]+=663.1;
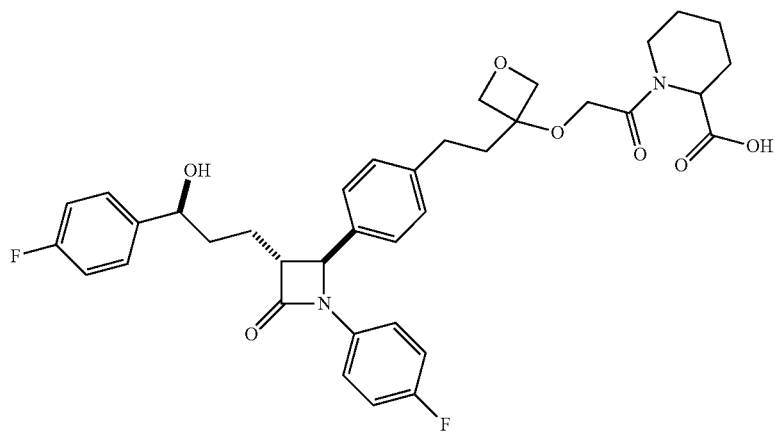 [SMILES: O=C(O)C1CCCCN1C(=O)COC1(CCc2ccc([C@@H]3[C@@H](CC[C@H](O)c4ccc(F)cc4)C(=O)N3c3ccc(F)cc3)cc2)COC1]
Example 24
(R)-2-(2-(3-((3-(4-((2S,3R)-1-(4-fluorophenyl)-3-((S)-3-(4-fluorophenyl)-3-hydroxypropyl)-4-oxoazetidin-2-yl)phenyl)propyl)(methyl)amino)oxetan-3-yl)acetamido)-3-methylbutanoic acid
$t_R$=3.29 min, [M+H]+=678.1;
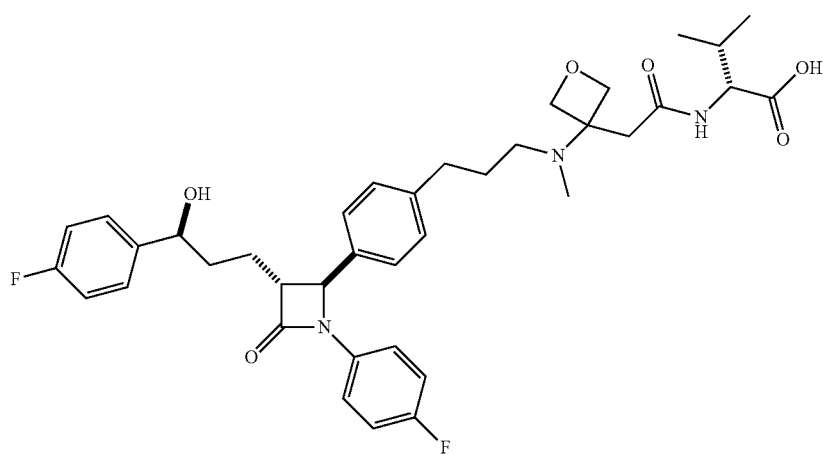 [SMILES: CC(C)[C@@H](NC(=O)CC1(N(C)CCCc2ccc([C@@H]3[C@@H](CC[C@H](O)c4ccc(F)cc4)C(=O)N3c3ccc(F)cc3)cc2)COC1)C(=O)O]

Example 25
(R)-2-(2-(3-(3-(4-((2S,3R)-1-(4-fluorophenyl)-3-((S)-3-(4-fluorophenyl)-3-hydroxypropyl)-4-oxoazetidin-2-yl)phenyl)propylamino)oxetan-3-yl)acetamido)-3-methylbutanoic acid
$t_R$=2.79 min, [M+H]+=664.1;
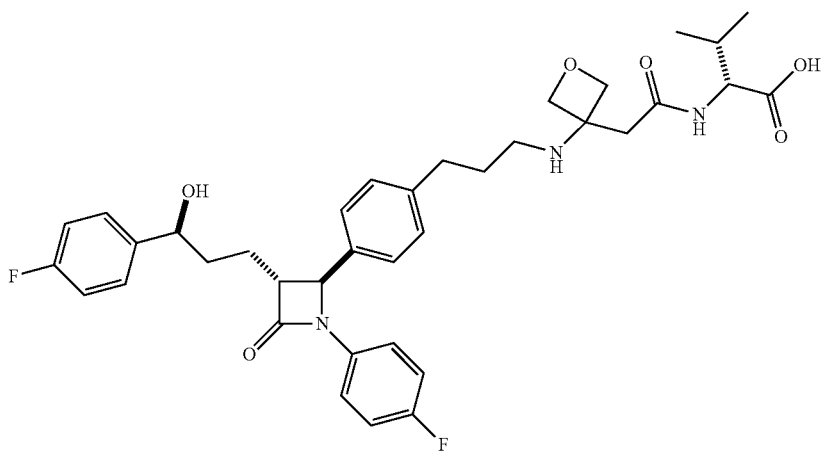 [SMILES: CC(C)[C@@H](NC(=O)CC1(NCCCc2ccc([C@@H]3[C@@H](CC[C@H](O)c4ccc(F)cc4)C(=O)N3c3ccc(F)cc3)cc2)COC1)C(=O)O]
Example 26
(R)-2-(2-(3-(3-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-3-methylbutanoic acid
$t_R$=3.02 min, [M+NH$_4$]+=669.1;
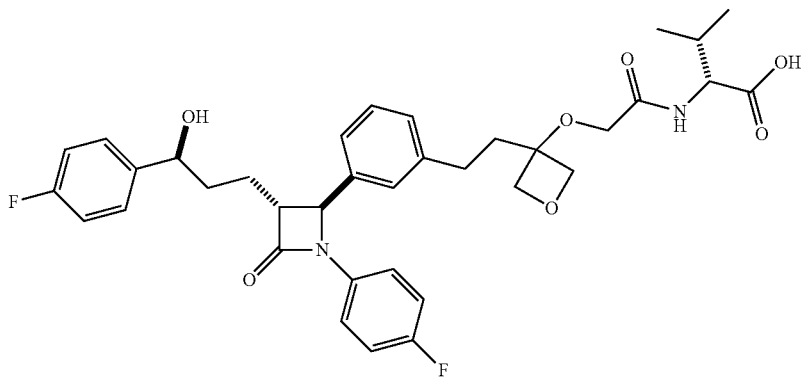 [SMILES: CC(C)[C@@H](NC(=O)COC1(CCc2cccc([C@@H]3[C@@H](CC[C@H](O)c4ccc(F)cc4)C(=O)N3c3ccc(F)cc3)c2)COC1)C(=O)O]

Example 27
(S)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-3-methylbutanoic acid
$t_R$=3.14 min, [M+H]+=651.1;
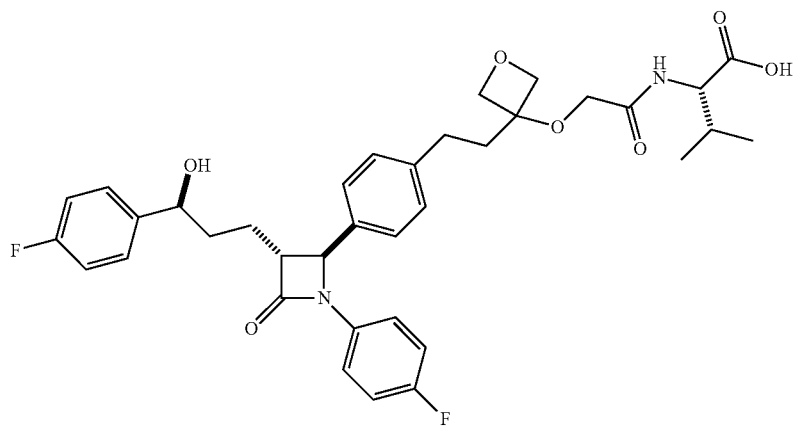 [SMILES: CC(C)[C@H](NC(=O)COC1(CCc2ccc([C@@H]3[C@@H](CC[C@H](O)c4ccc(F)cc4)C(=O)N3c3ccc(F)cc3)cc2)COC1)C(=O)O]
Example 28
2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)ethanesulfonic acid
$t_R$=2.58 min, [M−H]+NH$_4$+=677.1;
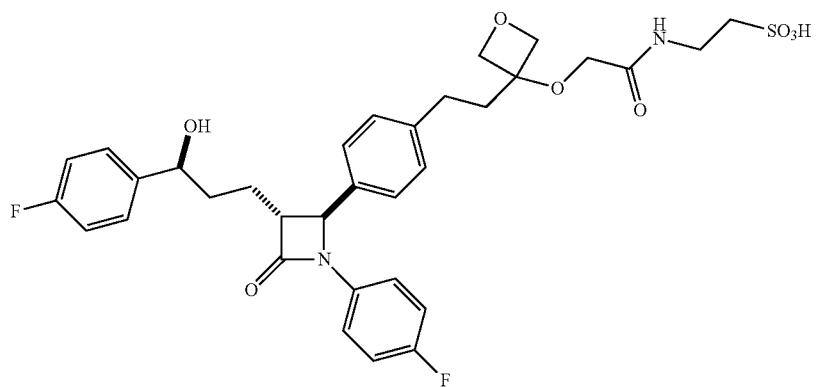 [SMILES: O=C(COC1(CCc2ccc([C@@H]3[C@@H](CC[C@H](O)c4ccc(F)cc4)C(=O)N3c3ccc(F)cc3)cc2)COC1)NCCS(=O)(=O)O]

Example 29
(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)methane-sulfonic acid
$t_R$=3.46 min, [M−H+NH$_4$]+=661.2;
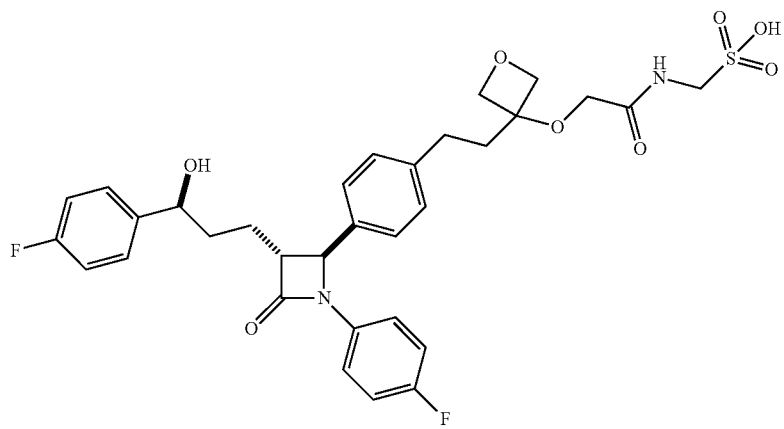 [SMILES: O=C(COC1(CCc2ccc([C@@H]3[C@@H](CC[C@H](O)c4ccc(F)cc4)C(=O)N3c3ccc(F)cc3)cc2)COC1)NCS(=O)(=O)O]
Example 30
1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-2-methylpropylphosphonic acid
$t_R$=2.64 min, [M+Na]+=709.0;
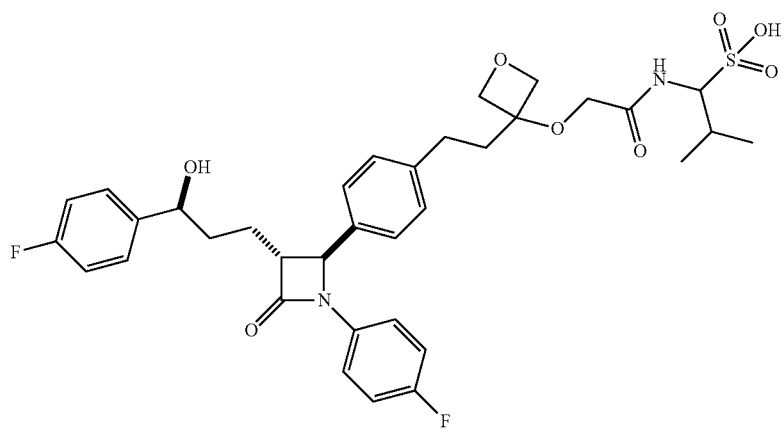 [SMILES: CC(C)C(NC(=O)COC1(CCc2ccc([C@@H]3[C@@H](CC[C@H](O)c4ccc(F)cc4)C(=O)N3c3ccc(F)cc3)cc2)COC1)S(=O)(=O)O]

Example 31
(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)methylphosphonic acid
$t_R$=2.70 min, [M+Na]+=667.1;
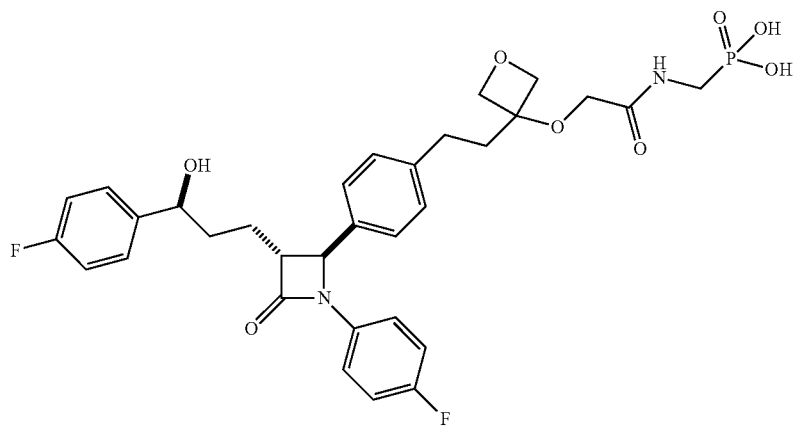 [SMILES: O=C(COC1(CCc2ccc([C@@H]3[C@@H](CC[C@H](O)c4ccc(F)cc4)C(=O)N3c3ccc(F)cc3)cc2)COC1)NCP(=O)(O)O]
Example 32
2,2'-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetylazanediyl)diacetic acid
$t_R$=2.70 min, [M+H]+=667.1;
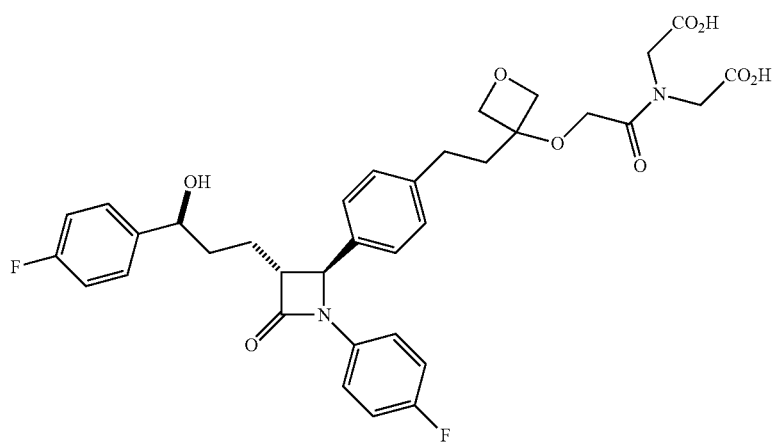 [SMILES: O=C(O)CN(CC(=O)O)C(=O)COC1(CCc2ccc([C@@H]3[C@@H](CC[C@H](O)c4ccc(F)cc4)C(=O)N3c3ccc(F)cc3)cc2)COC1]

Example 33
(R)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)succinic acid
$t_R$=3.29 min, [M+H]+=667.0;
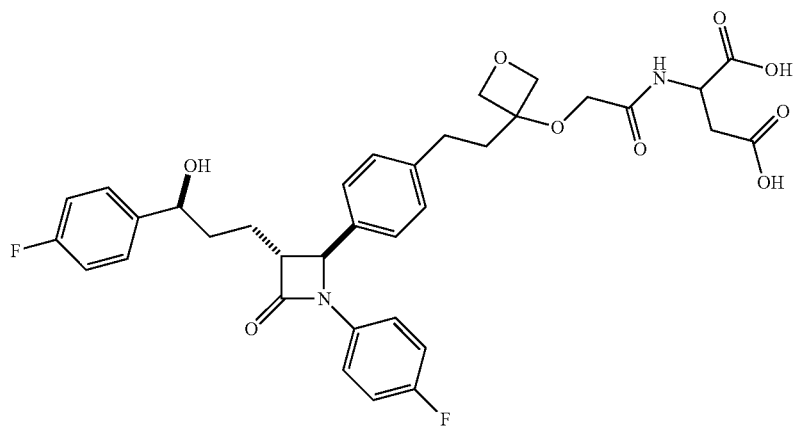 [SMILES: O=C(O)CC(NC(=O)COC1(CCc2ccc([C@@H]3[C@@H](CC[C@H](O)c4ccc(F)cc4)C(=O)N3c3ccc(F)cc3)cc2)COC1)C(=O)O]
Example 34
(R)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-3-hydroxypropanoic acid
$t_R$=2.83 min, [M+H]+=639.2;
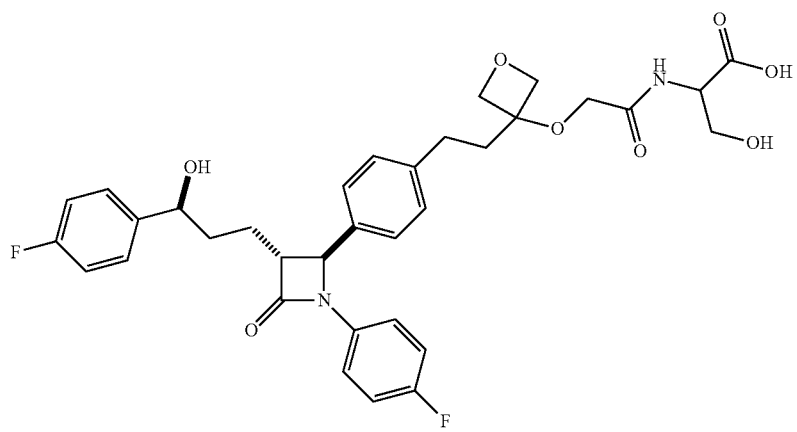 [SMILES: O=C(COC1(CCc2ccc([C@@H]3[C@@H](CC[C@H](O)c4ccc(F)cc4)C(=O)N3c3ccc(F)cc3)cc2)COC1)NC(CO)C(=O)O]

Example 35
1-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)cyclobutanecarboxylic acid
$t_R$=3.11 min, $[M+H]^+$=649.2;
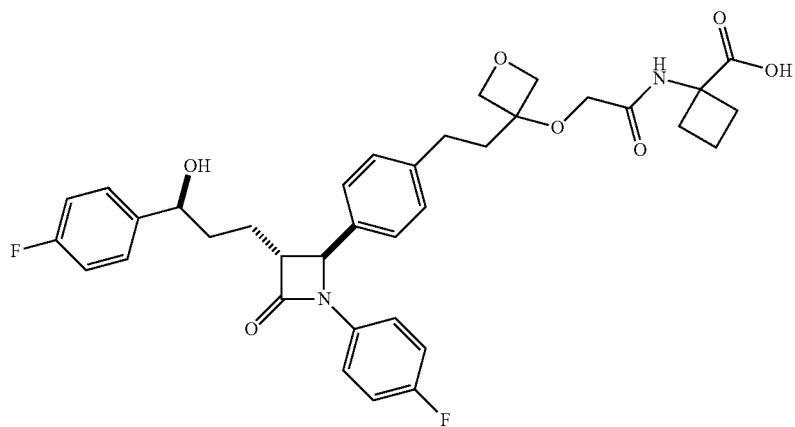 [SMILES: O=C(COC1(CCc2ccc([C@@H]3[C@@H](CC[C@H](O)c4ccc(F)cc4)C(=O)N3c3ccc(F)cc3)cc2)COC1)NC1(C(=O)O)CCC1]
Example 36
1-(2-(3-(4-((2S,3R)-1-(4-fluorophenyl)-3-((S)-3-fluorophenyl)-3-hydroxypropyl)-4-oxoazetidin-2-yl)phenethyl)oxetan-3-yloxy)acetamido)cyclopentanecarboxylic acid
$t_R$=3.15 min, $[M+H]^+$=662.9;
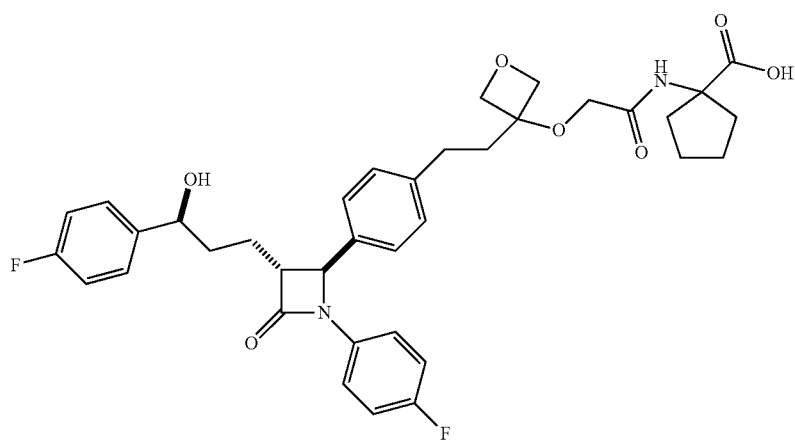 [SMILES: O=C(COC1(CCc2ccc([C@@H]3[C@@H](CC[C@H](O)c4ccc(F)cc4)C(=O)N3c3ccc(F)cc3)cc2)COC1)NC1(C(=O)O)CCCC1]

Example 37

2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-2-methylpropanoic acid $t_R$=3.19 min, [M+H]+=638.1

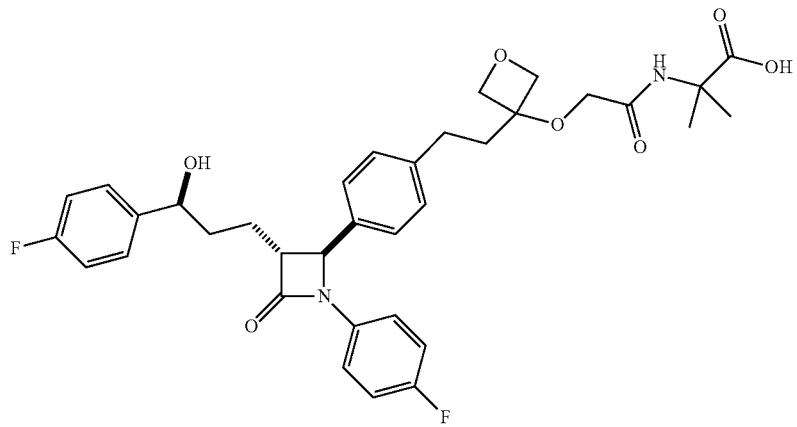 [SMILES: CC(C)(NC(=O)COC1(CCc2ccc([C@@H]3[C@@H](CC[C@H](O)c4ccc(F)cc4)C(=O)N3c3ccc(F)cc3)cc2)COC1)C(=O)O]

Example 38

2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamide $t_R$=2.68 min, [M−H+NH$_4$]+=567.0;

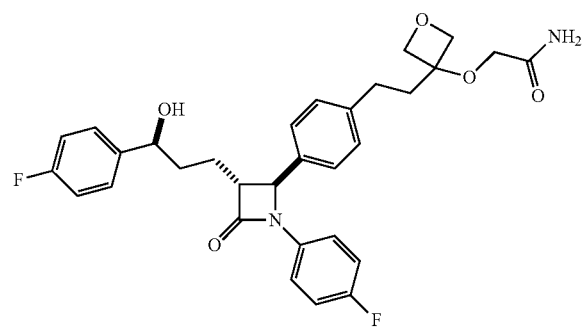 [SMILES: NC(=O)COC1(CCc2ccc([C@@H]3[C@@H](CC[C@H](O)c4ccc(F)cc4)C(=O)N3c3ccc(F)cc3)cc2)COC1]

Example 39

(R)-2-(2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamido)-3-methylbutanoic acid $t_R$=3.28 min, [M+H]+=651.1;

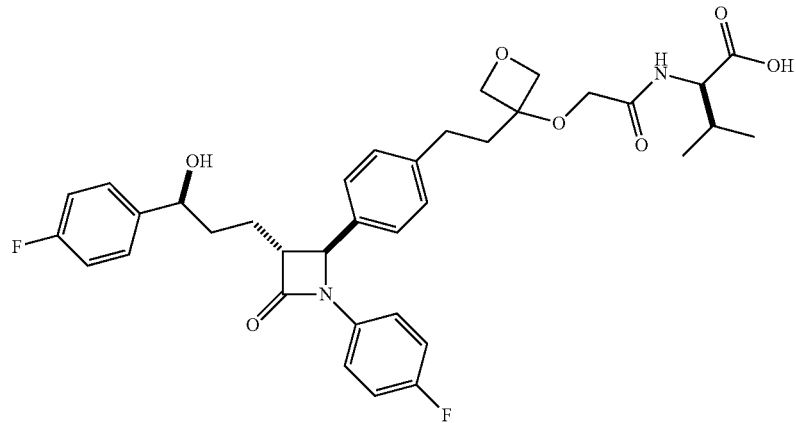

Example 40
(R)-1-(2-(3-(4-((2S,3R)-3-(2-(4-fluorophenoxy)ethyl)-1-(4-fluorophenyl)-4-oxoazetidin-2-yl)phenethyl)oxetan-3-yloxy)acetyl)pyrrolidine-2-carboxylic acid
$t_R$=3.23 min, [M+H]+=635.1;
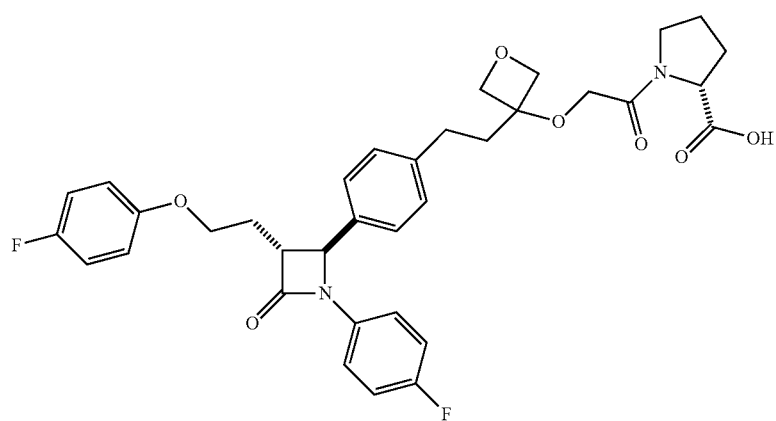 [SMILES: O=C(O)[C@H]1CCCN1C(=O)COC1(CCc2ccc([C@@H]3[C@@H](CCOc4ccc(F)cc4)C(=O)N3c3ccc(F)cc3)cc2)COC1]
Example 41
(R)-1-(2-(3-(4-((2S,3R)-1-(4-fluorophenyl)-3-(3-(4-fluorophenyl)-3-oxopropyl)-4-oxoazetidin-2-yl)phenethyl)oxetan-3-yloxy)acetyl)pyrrolidine-2-carboxylic acid
$t_R$=3.16 min, [M+H]+=647.1;
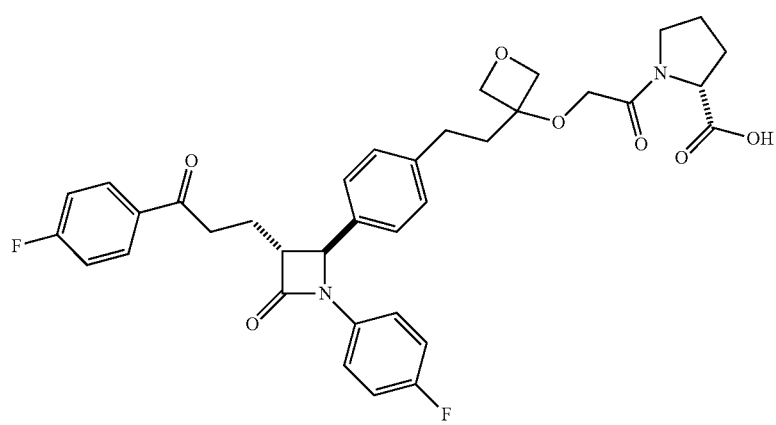 [SMILES: O=C(CC[C@H]1C(=O)N(c2ccc(F)cc2)[C@@H]1c1ccc(CCC2(OCC(=O)N3CCC[C@@H]3C(=O)O)COC2)cc1)c1ccc(F)cc1]

Example 42
(R)-2-(2-(3-(4-((2S,3R)-3-((S)-3-(4-fluorophenyl)-3-hydroxypropyl)-1-(4-(3-(methylsulfonamido)propyl)phenyl)-4-oxoazetidin-2-yl)phenethyl)oxetan-3-yloxy)acetamido)-3-methylbutanoic acid
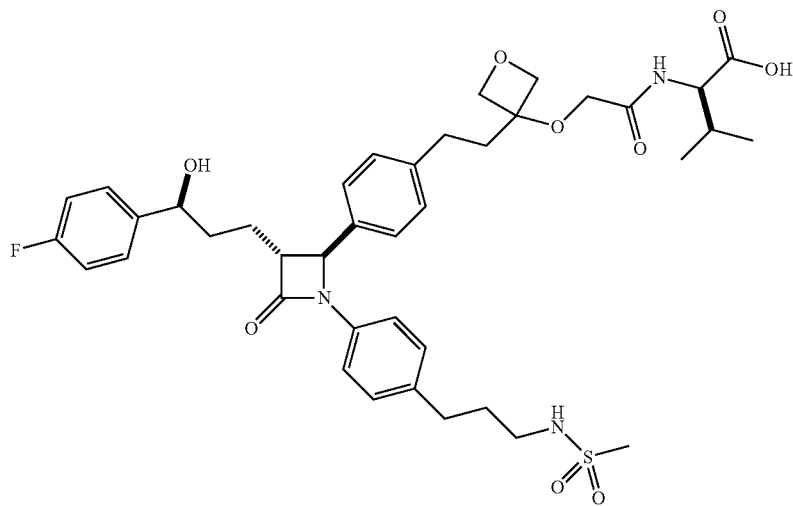 [SMILES: CC(C)[C@@H](NC(=O)COC1(CCc2ccc([C@@H]3[C@@H](CC[C@H](O)c4ccc(F)cc4)C(=O)N3c3ccc(CCCNS(C)(=O)=O)cc3)cc2)COC1)C(=O)O]
Example 43
(R)-2-(2-(3-(4-((2S,3R)-1-(4-(3-(1H-1,2,4-triazol-1-yl)propyl)phenyl)-3-((S)-3-(4-fluorophenyl)-3-hydroxypropyl)-4-oxoazetidin-2-yl)phenethyl)oxetan-3-yloxy)acetamido)-3-methylbutanoic acid
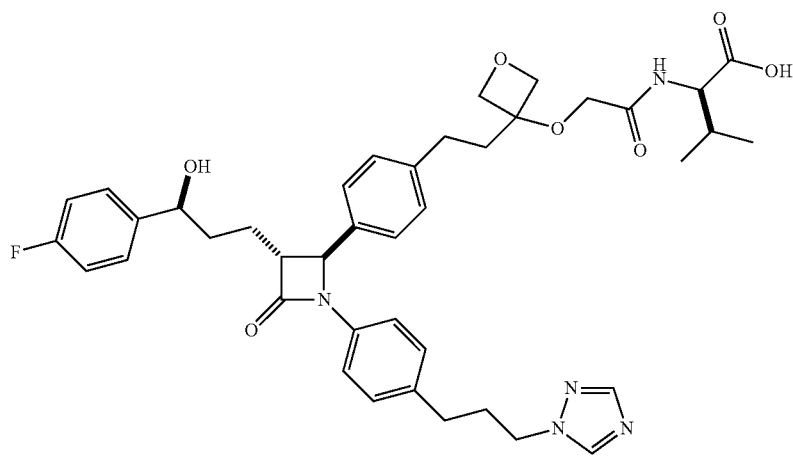 [SMILES: CC(C)[C@@H](NC(=O)COC1(CCc2ccc([C@@H]3[C@@H](CC[C@H](O)c4ccc(F)cc4)C(=O)N3c3ccc(CCCn4cncn4)cc3)cc2)COC1)C(=O)O]

Example 44
(R)-2-(2-(3-(4-((2S,3R)-3-((S)-3-(4-fluorophenyl)-3-hydroxypropyl)-4-oxo-1-(4-(3-(pyridin-2-ylamino)propyl)phenyl)azetidin-2-yl)phenethyl)oxetan-3-yloxy)acetamido)-3-methylbutanoic acid
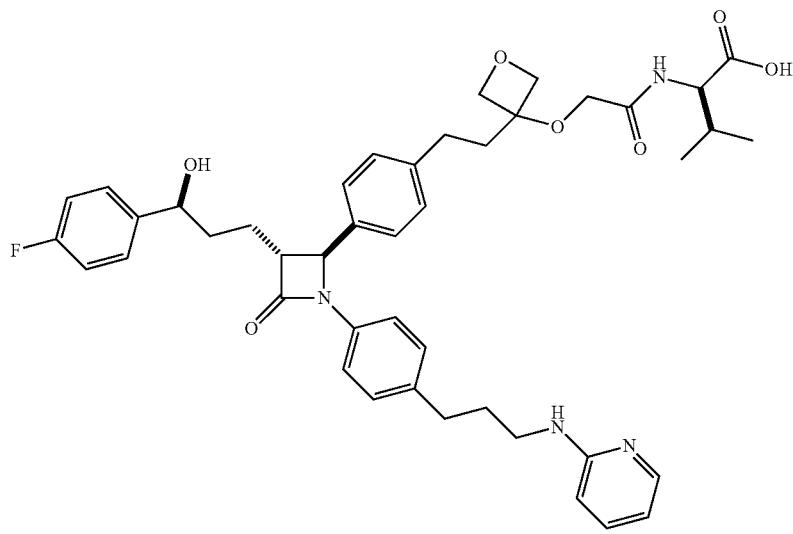 [SMILES: CC(C)[C@@H](NC(=O)COC1(CCc2ccc([C@@H]3[C@@H](CC[C@H](O)c4ccc(F)cc4)C(=O)N3c3ccc(CCCNc4ccccn4)cc3)cc2)COC1)C(=O)O]
Example 45
(R)-2-(2-(3-(4-((2S,3R)-3-((S)-3-(4-fluorophenyl)-3-hydroxypropyl)-1-(4-(3-(oxazol-2-ylamino)propyl)phenyl)-4-oxoazetidin-2-yl)phenethyl)oxetan-3-yloxy)acetamido)-3-methylbutanoic acid
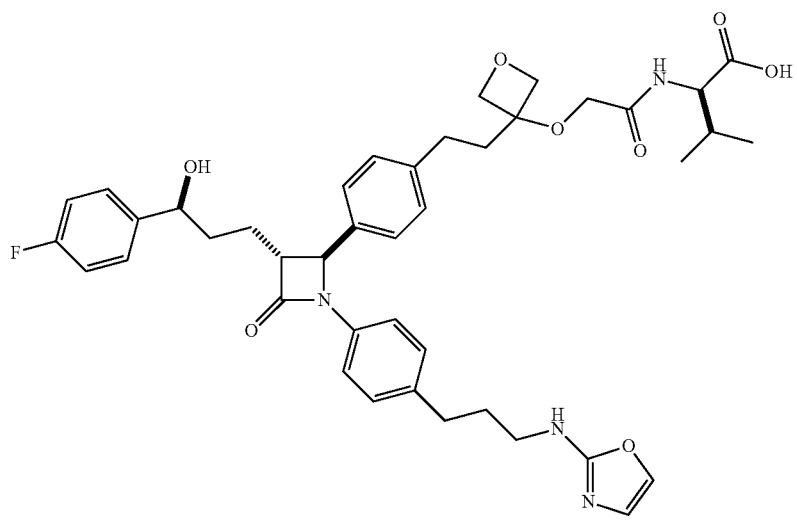 [SMILES: CC(C)[C@@H](NC(=O)COC1(CCc2ccc([C@@H]3[C@@H](CC[C@H](O)c4ccc(F)cc4)C(=O)N3c3ccc(CCCNc4ncco4)cc3)cc2)COC1)C(=O)O]

Example 46

N-(1,3-dihydroxy-2-(hydroxymethyl)propan-2-yl)-2-(3-(4-((2S,3R)-1-(4-fluorophenyl)-3-((S)-3-(4-fluorophenyl)-3-hydroxypropyl)-4-oxoazetidin-2-yl)phenethyl)oxetan-3-yloxy)acetamide $t_R$=2.89 min, [M+H]+=655.1;

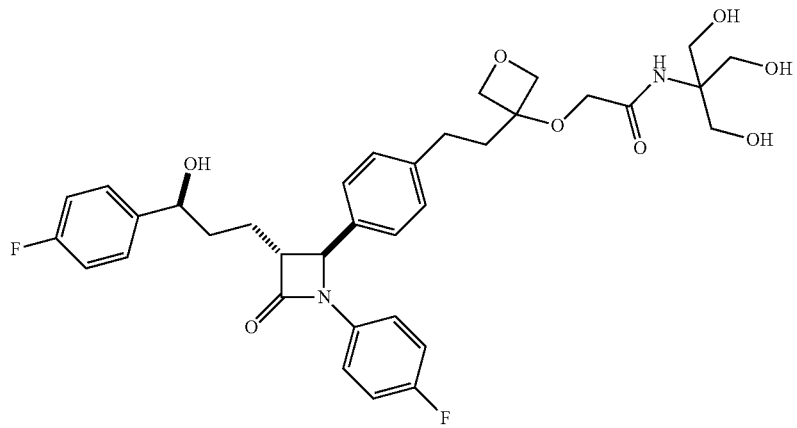 [SMILES: O=C(COC1(CCc2ccc([C@@H]3[C@@H](CC[C@H](O)c4ccc(F)cc4)C(=O)N3c3ccc(F)cc3)cc2)COC1)NC(CO)(CO)CO]

Example 47

Accute Cholesterol Absorption Inhibition Assay in Mice

Compounds were added to a solution of 0.5% Methylcellulose (Sigma)/5% Solutol, BASF) or another suitable vehicle at a concentration of 0.1-1 mg/ml. C56BL/6 mice (n=3-6/group), aged 6-8 weeks were dosed orally with 0.1 ml of vehicle or 0.1 mL of vehicle containing the test compound (0.5-5 mg/kg) or ezetimibe (10 mg/kg) as positive control. Thirty minutes later all of the mice were dosed orally with 0.1 mL corn oil containing 2 μCi [$^3$H]-cholesterol per mouse. Two hours after administration of radiolabeled cholesterol, the animals were euthanized and blood collected. Cholesterol counts in plasma were determined, and percent inhibition of cholesterol absorption was calculated relative to the vehicle control.

TABLE 1

Efficacy in mice: representative examples

| Compound | Dose | Cholesterol Absorption Inhibition (%) |
|---|---|---|
| Example 1 | 1 mg/kg | 87 |
| Example 19 | 1 mg/kg | 83 |
| Example 20 | 1 mg/kg | 42 |
| Example 22 | 1 mg/kg | 80 |
| Example 23 | 1 mg/kg | 73 |
| Example 28 | 1 mg/kg | 63 |
| Example 39 | 1 mg/kg | 82 |
| Ezetimibe | 10 mg/kg | 87 |

Example 48

Long-Term LDL Lowering in Syrian Golden Hamsters

Groups of 6 male hamsters weighing 90±10 g are fed a high fat diet (g/100 g: corn oil, 5; coconut oil, 5; cholesterol, 0.2; standard chow, 89.8) for 7 days. Afterwards vehicle or test compounds (3-10 mg/kg bw/day) in a solution of 0.5% Methylcellulose, 5% Solutol or another suitable vehicle are administered at least three times daily for 14 consecutive days. Following an overnight fasting period, blood serum is obtained from the retro-orbital sinus of each animal on day 0 (7 days after initiating of the high fat diet) and on days 8 and 15 after dosing for 7 and 14 days. The serum is assayed for total cholesterol, LDL-cholesterol, HDL-cholesterol and triglycerides. The percent change of treated relative to the vehicle control group is determined.

TABLE 2

Efficacy in Hamster: representative examples

| Compound | Dose (mg/kg/day) | LDL reduction @ day 14 (%) |
|---|---|---|
| Example 34 | 3 × 1 | 76 |
| Example 35 | 3 × 1 | 80 |
| Example 39 | 3 × 1 | 74 |
| Example 46 | 3 × 1 | 67 |

Example 49

Determination of Absorption

The permeability of the compounds of the present invention was determined using the Cloe Screen® (unidirectional Cloe Screen MDR1-MDCK permeability assay; Cyprotex) and is expressed by $P_{app}$ (cm·s$^{-1}$). Caco-2 cells are widely used as an in vitro model for predicting human drug absorption. The Caco-2 cell line is derived from a human colorectal carcinoma, and when cultured, the cells spontaneously differentiate into monolayers of polarised enterocytes. The cells are typically seeded on Transwell™ plates and form a confluent monolayer over 20 days prior to the experiment. On day 20, the test compound is added to the apical side of the membrane and the transport of the compound across the monolayer is monitored over a 2 hour time period. The permeability coefficient ($P_{app}$) is calculated from the equation: $P_{app} = (dQ/dt)/(C_0 \times A)$, where (dQ/dt) is the rate of permeation of the drug across the cells, $C_0$ is the donor compartment concentration at time zero and A is the area of the cell monolayer.

TABLE 3

Impermeability: representative examples

| Compound | $P_{app}$ in cm·s$^{-1}$ |
|---|---|
| Example 1 | $1.68 \times 10^{-6}$ |
| Example 19 | $0.14 \times 10^{-6}$ |
| Example 34 | $0.57 \times 10^{-6}$ |
| Example 35 | $0.73 \times 10^{-6}$ |
| Example 39 | $0.92 \times 10^{-6}$ |
| Example 46 | $1.09 \times 10^{-6}$ |
| Ezetimibe | $46 \times 10^{-6}$ |

The invention claimed is:

1. A compound according to formula I or a pharmaceutically acceptable salt thereof,

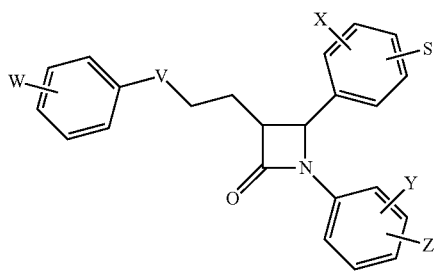

I wherein
- W, X and Y represent, independently of each other, H, —(C1-C10)alkyl, —OH, —O(C1-C10)alkyl, -aryl, halogen, —CF₃;
- Z represents H, —(C1-C10)alkyl, —(C1-C10)alkenyl, —(C1-C10)alkynyl, aryl, a polar group A, or combinations thereof, wherein the —(C1-C10)alkyl, —(C1-C10)alkenyl, —(C1-C10)alkynyl, or aryl, may be substituted by at least one polar group A,
  - wherein A is selected from halogen, epoxy, —COR₆, —COOR₇, —NR₈R₉, —N⁺R₈R₉R₁₀, —OR₁₁, —CONR₁₂R₁₃, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S,
  - wherein R₆, R₇, R₈, R₉, R₁₀, R₁₁, R₁₂, R₁₃ are independently of each other H, (C1-C10)alkyl, aryl or heteroaryl;
- V represents —CH₂—, —CH(OH)—, —C(=O)—, —O—, NR₄, —C(CH₂OCH₂)— wherein R₄ represents H, (C1-C10)alkyl or aryl;

S is a group of formula IIIa or IIIb

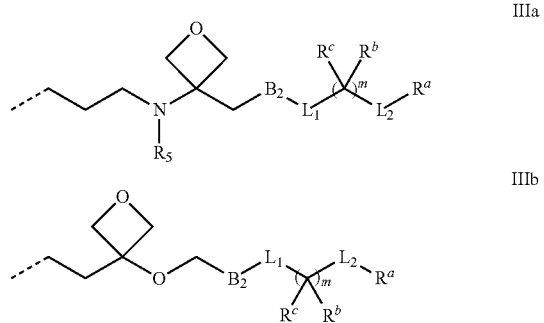

wherein
- B₂ represents —C(O)NR$^d$—, —C(O)O—, aryl or heteroaryl;
- R₅ is H or (C1-C6)alkyl;
- R$^a$, R$^d$ represent (i) independently of each other H, (C1-C10)alkyl, cycloalkyl, aryl, or a polar group A selected from halogen, epoxy, —COR₆, —COOR₇, —NR₈R₉, —N⁺R₈R₉R₁₀, —OR₁₁, —CONR₁₂R₁₃, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S, wherein R₆, R₇, R₈, R₉, R₁₀, R₁₁, R₁₂, R₁₃ are independently of each other H, (C1-C10)alkyl, aryl, or heteroaryl, or (ii) R$^a$ and R$^d$ form together a N-containing 5- or 6-membered heteroaryl or heterocycloalkyl;
- L₁, L₂ represent independently of each other a covalent bond, a 5- or 6-membered arylgroup or a group —(CH₂)$_p$—, wherein p is 1, 2 or 3;
- R$^b$, R$^c$ represent (i) independently of each other H, (C1-C10)alkyl, cycloalkyl, aryl, or a polar group A selected from halogen, epoxy, —COR₆, —COOR₇, —NR₈R₉, —N⁺R₈R₉R₁₀, —OR₁₁, —CONR₁₂R₁₃, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S, wherein R₆, R₇, R₈, R₉, R₁₀, R₁₁, R₁₂, R₁₃ are independently of each other H, (C1-C10)alkyl, aryl, or heteroaryl, or (ii) R$^b$ and R$^c$ form together a (C3-C6)cycloalkyl or (C3-6)heterocycloalkyl, and
- m is 0, 1 or 2;

with the proviso that at least one of groups R$^a$, R$^b$, R$_c$, R$^d$ is a polar group A.

2. The compound according to claim 1 wherein V is CH(OH), —C(=O)— or —O— and/or wherein W, X, Y and Z independently represent H, halogen, or —OH.

3. The compound according to claim 1 wherein Z is H and Y is —F in para position.

4. The compound according to claim 1, wherein B₂ represents —C(O)NR$^d$—, —C(O)O—, or a five-membered heteroaryl having two heteroatoms selected from N, O or S.

5. The compound according to claim 1 having the formula VIa, VIb, VIc or formula VIIa, VIIb, VIIc or a pharmaceutically acceptable salt thereof,

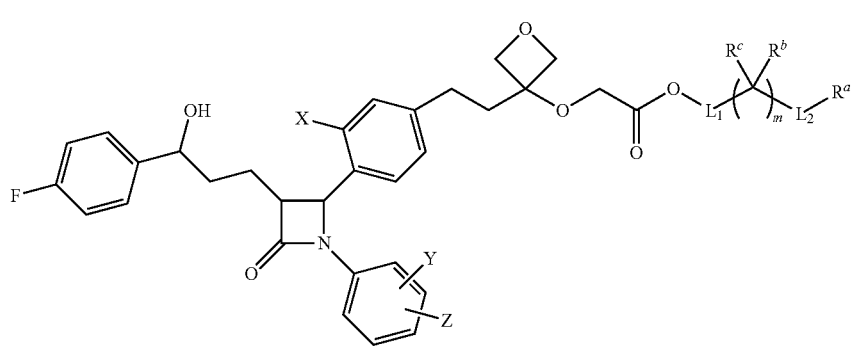 VIa
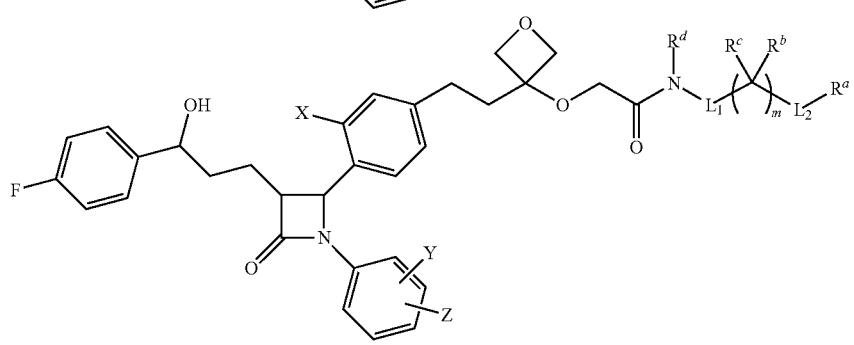 VIb
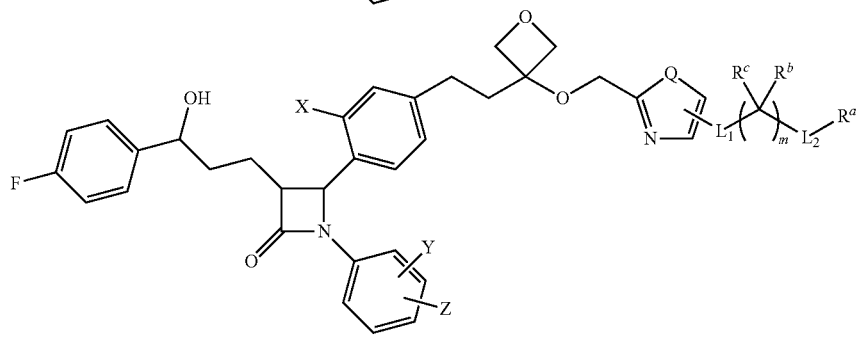 VIc
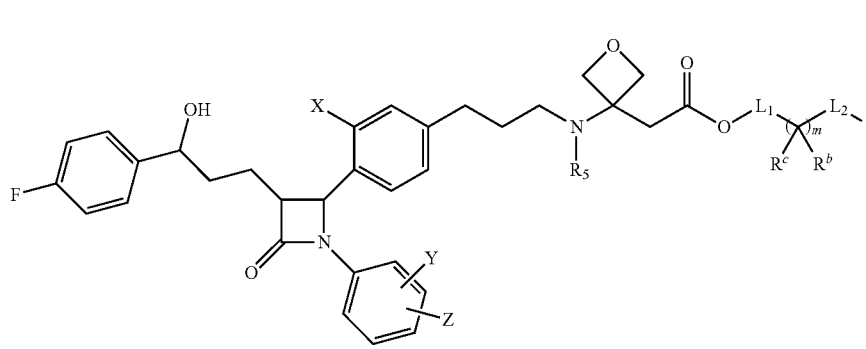 VIIa
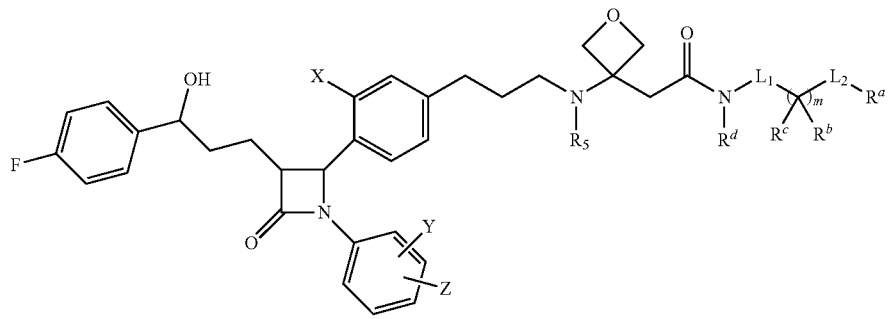 VIIb

VIIc

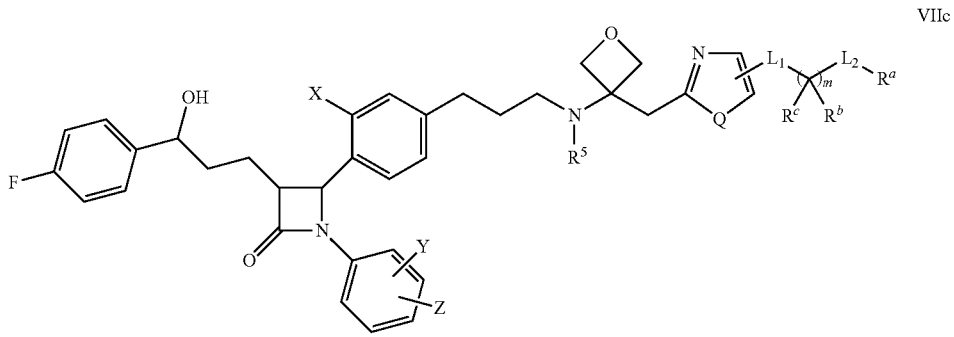

wherein
X, Y are, independently of each other, H, OH or F;
Z represents H, —(C1-C10)alkyl, —(C1-C10)alkenyl, —(C1-C10)alkynyl, aryl, a polar group A, or combinations thereof, wherein the —(C1-C10)alkyl, —(C1-C10)alkenyl, —(C1-C10)alkynyl, or aryl, may be substituted by at least one polar group A,
wherein A is selected from halogen, epoxy, —$COR_6$, —COORS, —$NR_8R_9$, —$N^+R_8R_9R_{10}$, —$OR_{11}$, —$CONR_{12}R_{13}$, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S,
wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl;
Q is —O—, —$NR_5$—, —S—,
m is 0, 1 or 2;
$L_1$, $L_2$ represent independently of each other a covalent bond, a 5- or 6-membered arylgroup or a group —$(CH_2)_p$—, wherein p is 1, 2 or 3;
$R_5$ is H, (C1-C6)alkyl, benzyl or aryl;
$R^a$, $R^d$ represent (i) independently of each other H, (C1-C10)alkyl, cycloalkyl, aryl, or a polar group A selected from halogen, epoxy, —$COR_6$, —$COOR_7$, —$NR_8R_9$, —$N^+R_8R_9R_{10}$, —$OR_{11}$, —$CONR_{12}R_{13}$, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or (ii) $R^a$ and $R^d$ form together a N-containing 5- or 6-membered heteroaryl or heterocycloalkyl;
$R^b$, $R^c$ represent (i) independently of each other H, (C1-C10)alkyl, cycloalkyl, aryl, a polar group A, or combinations thereof,
wherein A is selected from halogen, epoxy, —$COR_6$, —$COOR_7$, —$NR_8R_9$, —$N^+R_8R_9R_{10}$, —$OR_{11}$, —$CONR_{12}R_{13}$, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S,
wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, or (ii) $R^b$ and $R^c$ form together a (C3-C6)cycloalkyl or (C3-6)heterocycloalkyl;
with the proviso that at least one of groups $R^a$, $R^b$, $R^c$, $R^d$ is a polar group A.

6. The compound according to claim 1 wherein (i) $L_1$ is —$(CH_2)_p$—, wherein p is 1, 2 or 3 and $L_2$ is a covalent bond, or (ii) $L_1$ is a covalent bond and $L_2$ is a 5- or 6-membered aryl group.

7. The compound according to claim 1 having formula VIIIa or VIIIb

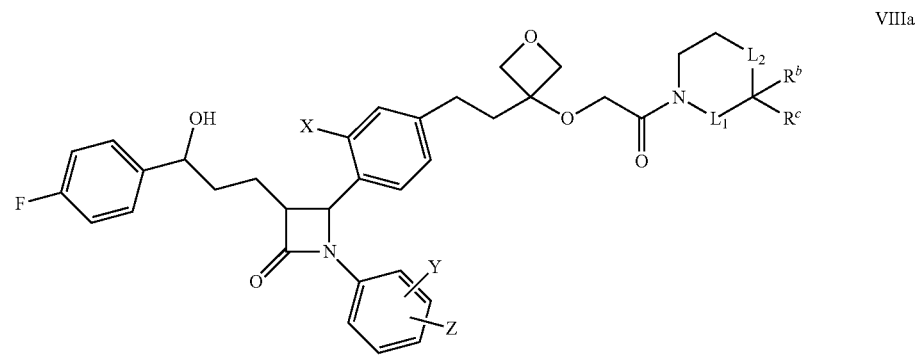

VIIIa

-continued

VIIIb

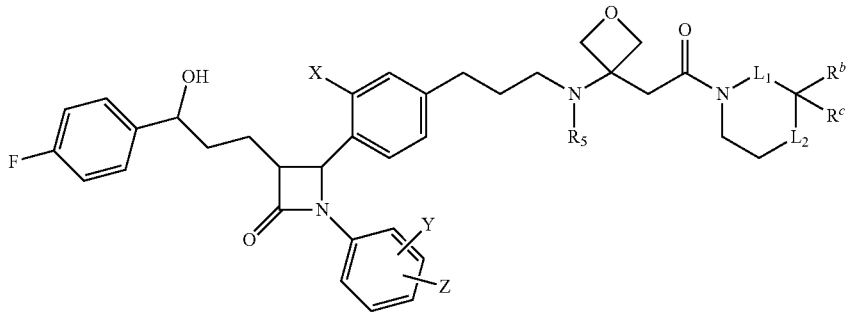

wherein

X, Y are independently of each other, H, OH or F;

Z represents H, —(C1-C10)alkyl, —(C1-C10)alkenyl, —(C1-C10)alkynyl, aryl, a polar group A, or combinations thereof, wherein the —(C1-C10)alkyl, —(C1-C10)alkenyl, —(C1-C10)alkynyl, or aryl, may be substituted by at least one polar group A, wherein A is selected from halogen, epoxy, —$COR_6$, —$COOR_7$, —$NR_8R_9$, —$N^+R_8R_9R_{10}$, —$OR_{11}$, —$CONR_{12}R_{13}$, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl;

$R^b$, $R^c$ represent independently of each other H, (C1-C10) alkyl, cycloalkyl, aryl, or a polar group A selected from halogen, epoxy, —$COR_6$, —$COOR_6$, —$NR_8R_9$, —$N^+R_8R_9R_{10}$, —$OR_{11}$, —$CONR_{12}R_{13}$, phosphate groups, phosphonate groups, sulfonate groups, sulfonyl groups, sulfonamides, polyhydroxy, a 4- to 7-membered heteroaryl or 4- to 7-membered heterocycloalkyl each having 1 to 4 ring atoms selected from N, O, S, wherein $R_6$, $R_7$, $R_8$, $R_9$, $R_{10}$, $R_{11}$, $R_{12}$, $R_{13}$ are independently of each other H, (C1-C10)alkyl, aryl, or heteroaryl, $L_1$, $L_2$ represent independently of each other a covalent bond or —$(CH_2)_p$—, wherein p is 1, 2 or 3, and $R_5$ is H or (C1-C6)alkyl, benzyl or aryl.

8. The compound according to claim 1 wherein $R^b$ and $R^c$ are a C3- or C4-cycloalkyl or an oxetane.

9. The compound according to claim 1 wherein the substituents at the 3- and 4-position of the β-lactam ring are in trans configuration to each other.

10. A pharmaceutical composition comprising a therapeutically effective amount of a compound of claim 1 with a pharmaceutically acceptable carrier, optionally further comprising one or more additional active agents.

11. A method for treating or reducing the risk of developing arthrosclerosis or for the reduction of cholesterol levels comprising administering to a subject in need of such treatment an effective amount of a compound according to claim 1 or a pharmaceutical composition according to claim 10.

12. The compound according to claim 1, wherein Z is —(C1-C10)alkyl, —(C1-C10)alkenyl, —(C1-C10)alkynyl, or aryl, substituted by at least one polar group A.

\* \* \* \* \*